US012465695B2

(12) United States Patent
Heinrich et al.

(10) Patent No.: US 12,465,695 B2
(45) Date of Patent: Nov. 11, 2025

(54) DATA COLLECTION APPARATUS FOR ATTACHMENT TO AN INJECTION DEVICE

(71) Applicant: Sanofi, Paris (FR)

(72) Inventors: Alexander Heinrich, Wil (CH); Sven Zwicker, Wil (CH)

(73) Assignee: Sanofi, Paris (FR)

(*) Notice: Subject to any disclaimer, the term of this patent is extended or adjusted under 35 U.S.C. 154(b) by 1181 days.

(21) Appl. No.: 17/267,377

(22) PCT Filed: Aug. 9, 2019

(86) PCT No.: PCT/EP2019/071409
§ 371 (c)(1),
(2) Date: Feb. 9, 2021

(87) PCT Pub. No.: WO2020/035406
PCT Pub. Date: Feb. 20, 2020

(65) Prior Publication Data

US 2021/0290854 A1 Sep. 23, 2021

(30) Foreign Application Priority Data

Aug. 15, 2018 (EP) .................................... 18306121

(51) Int. Cl.
*A61M 5/31* (2006.01)
*A61M 5/315* (2006.01)
*G16H 20/17* (2018.01)

(52) U.S. Cl.
CPC .... *A61M 5/31551* (2013.01); *A61M 5/31585* (2013.01); *G16H 20/17* (2018.01); *A61M 2205/52* (2013.01); *A61M 2205/8206* (2013.01)

(58) Field of Classification Search
CPC .......... A61M 5/31585; A61M 5/31551; A61M 2205/52; A61M 2205/8206;
(Continued)

(56) References Cited

U.S. PATENT DOCUMENTS

| | | | | |
|---|---|---|---|---|
| 11,052,197 B2 | 7/2021 | Wang | | |
| 2016/0045666 A1* | 2/2016 | Wilden | ............ | A61M 5/31541<br>604/207 |

(Continued)

FOREIGN PATENT DOCUMENTS

| | | |
|---|---|---|
| CN | 1374876 | 10/2002 |
| CN | 102596292 | 7/2012 |

(Continued)

OTHER PUBLICATIONS

PCT International Preliminary Report on Patentability in International Application No. PCT/EP2019/071409, dated Feb. 16, 2021, 7 pages.

(Continued)

*Primary Examiner* — Laura A Bouchelle
*Assistant Examiner* — Anna E Goldberg-Richmeier
(74) *Attorney, Agent, or Firm* — Bond, Schoeneck & King, PLLC

(57) ABSTRACT

A data collection device comprising a first portion configured for attachment to a rotatable dosage knob of an injection device, and a second portion rotatably coupled with the first portion, wherein at least part of the second portion is movable axially relative to the first portion. The second portion comprises a button which is rotationally fixed relative to the second portion, and moveable between an extended position and a depressed position, wherein moving the button to the depressed position causes the second portion to move axially relative to the first portion. The device comprises a one-way mechanism engageable with the first portion and configured to permit relative rotational movement between the button and the first portion in a first
(Continued)

rotational direction and to prevent relative rotational movement between the button and the first portion in a second rotational direction opposite the first rotational direction.

20 Claims, 13 Drawing Sheets

(58) Field of Classification Search
CPC ...... A61M 2005/3126; A61M 5/31528; A61M 5/31533; A61M 5/31548; A61M 5/3155; A61M 5/31553; A61M 5/3156; A61M 5/31556; G16H 20/17
See application file for complete search history.

(56) References Cited

U.S. PATENT DOCUMENTS

| | | | | |
|---|---|---|---|---|
| 2016/0287804 | A1* | 10/2016 | Madsen | G01D 5/1655 |
| 2016/0303326 | A1 | 10/2016 | Binier | |
| 2018/0050155 | A1* | 2/2018 | Avery | A61M 5/31541 |
| 2018/0154086 | A1* | 6/2018 | Toporek | A61M 5/31551 |

FOREIGN PATENT DOCUMENTS

| | | | |
|---|---|---|---|
| CN | 105749383 | | 7/2016 |
| CN | 106039477 | | 10/2016 |
| CN | 107206184 | | 9/2017 |
| JP | 2018-511384 | A | 4/2018 |
| JP | 2018-517502 | A | 7/2018 |
| WO | WO 2001/019434 | | 3/2001 |
| WO | WO 2011/026928 | | 3/2011 |
| WO | WO 2013/058698 | | 4/2013 |
| WO | WO 2016/128425 | | 8/2016 |
| WO | WO 2018/104289 | | 6/2018 |
| WO | WO 2018/104289 | A1 | 6/2018 |

OTHER PUBLICATIONS

PCT International Search Report and Written Opinion in International Application No. PCT/EP2019/071409, dated Sep. 11, 2019, 9 pages.

* cited by examiner

DATA COLLECTION APPARATUS FOR ATTACHMENT TO AN INJECTION DEVICE

CROSS REFERENCE TO RELATED APPLICATIONS

The present application is the national stage entry of International Patent Application No. PCT/EP2019/071409, filed on Aug. 9, 2019, and claims priority to Application No. EP 18306121.7, filed on Aug. 15, 2018, the disclosures of which are incorporated herein by reference.

TECHNICAL FIELD

The present disclosure relates to a data collection device for attachment to an injection device.

BACKGROUND

A variety of diseases exists that require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning a dosage knob and observing the actual dose from a dose window or display of the insulin pen. The dose is then injected by inserting the needle into a suited skin portion and pressing an injection button of the insulin pen. To be able to monitor insulin injection, for instance to prevent false handling of the insulin pen or to keep track of the doses already applied, it is desirable to measure information related to a condition and/or use of the injection device, such as for instant information on the injected insulin dose.

SUMMARY

A first aspect of the present disclosure provides a data collection device comprising a first portion configured for attachment to a rotatable dosage knob of an injection device in which the dosage knob is configured to rotate as medicament is expelled from the injection device, a second portion rotatably coupled with the first portion, wherein at least part of the second portion is movable axially relative to the first portion, the second portion comprising a button which is rotationally fixed relative to the second portion, and moveable between an extended position and a depressed position, the button and second portion configured such that moving the button to the depressed position causes the second portion to move axially relative to the first portion, a sensor arrangement configured to detect rotation of the first portion relative to the second portion, and a processor arrangement configured to, based on said detected movement, determine a medicament amount expelled by the injection device, wherein the data collection device comprises a one-way mechanism engageable with the first portion and configurable to permit relative rotational movement between the button and the first portion in a first rotational direction and to prevent relative rotational movement between the button and the first portion in a second rotational direction opposite to the first rotational direction.

The one-way mechanism may comprise a ratchet surface formed on one of the first portion and the second portion or button, and at least one follower element engageable with the ratchet surface and formed on the other of the first portion and the second portion or button.

The at least one follower element may be biased into engagement with the ratchet surface at least when the button is in the depressed position, and the at least one follower element may be deflectable by movement across the ratchet surface.

The at least one follower element may comprise a resilient arm. The at least one follower element may bias the button towards the extended position. The ratchet surface may be formed on the button. The ratchet surface may be formed on a radially inwardly-facing surface of the button or may be formed on an axially-facing end wall of the button. The ratchet surface may be formed on an inside wall of the first portion.

The follower element may be provided on a follower member which is a separate component to the first and second portions. The follower member may be fixedly secured to the first portion.

The follower member may be connected to the button so as to be axially fixed relative to the button but rotatable relative to the button.

The follower member may be connected to the button so as to be axially and rotatably fixed relative to the button.

The follower member may comprise a battery holder.

The second portion may be disposed at least partially within, and coaxial with the first portion of the data collection device.

The button may extend further out of first portion in extended position than in depressed position.

The follower element may be integrally formed with first portion. The follower element may be a component which snap-fits into button or second portion. The button or second portion and follower element may each have cooperating connection elements to enable connection of the button or second portion and follower element.

The follower element may comprise a ring-shaped body with arms extending therefrom. Pawl element may extend axially and/or radially from an arm of the ring-shaped body. The pawl element may be metallic or may be plastic.

The sensor arrangement may comprise one or more of an optical sensor, a magnetic sensor, a capacitive sensor and a mechanical sensor.

The device may comprise a biasing member configured to bias the button into the extended position.

The one-way mechanism may be configurable between an engaged position in which rotation of button relative to the first portion in the second rotational direction is prevented, and a disengaged position in which the button is freely rotatable relative to first portion, and wherein movement of button from extended position towards the depressed position moves the one-way mechanism from the disengaged position to engaged position.

When the one-way mechanism is in the engaged position, the follower element may be in engagement with ratchet surface, and when the one-way mechanism is in the disengaged position, the follower element may be out of engagement with ratchet surface.

The device may comprise a power source and a switch configured to connect the power source to the processor arrangement to render the device between a deactivated state and an activated state, and movement of the button towards the depressed position may operate the switch to render device in the activated state.

A further aspect of the present disclosure provides a medicament administration apparatus comprising an injection device comprising a rotatable component configured to rotate as a medicament is expelled from the injection device, and a data collection device as defined above.

The injection device may comprise an injection button arranged to cause expulsion of the medicament from the injection device, and the second portion of the data collection device may be arranged to press on the injection button when pressure is applied to the button of the data collection device.

The medicament administration apparatus may comprise a syringe, cartridge or other container of medicament within the injection device.

BRIEF DESCRIPTION OF THE FIGURES

Example embodiments will now be described with reference to the accompanying figures, in which.

DETAILED DESCRIPTION

The present specification discloses a data collection device which is attachable to a proximal end of an injection device, such as a pen injector, such as to fit the injector device like a cap. The data collection device is configured such that it can be push-fitted over a dosage knob or dose dialing knob of the injection device. In particular, a first portion of the data collection device includes a cavity that is configured to receive and securely fit over the dose setting dial. The data collection device can easily be installed on and removed from the injection device, such as by push fit or other appropriate cooperating features of the data collection device and dose setting dial. When installed, the data collection device is manipulated by the user in order to effect operation of the injection device and monitors quantities and times of medicament delivery from the injection device. Medicament quantities can be transmitted, e.g. to a smartphone, and/or displayed on a display of the data collection device.

In the following disclosure, embodiments will be described with reference to an insulin injection device. The present disclosure is however not limited to such application and may equally well be deployed with injection devices that eject other medicaments.

Figure 1:
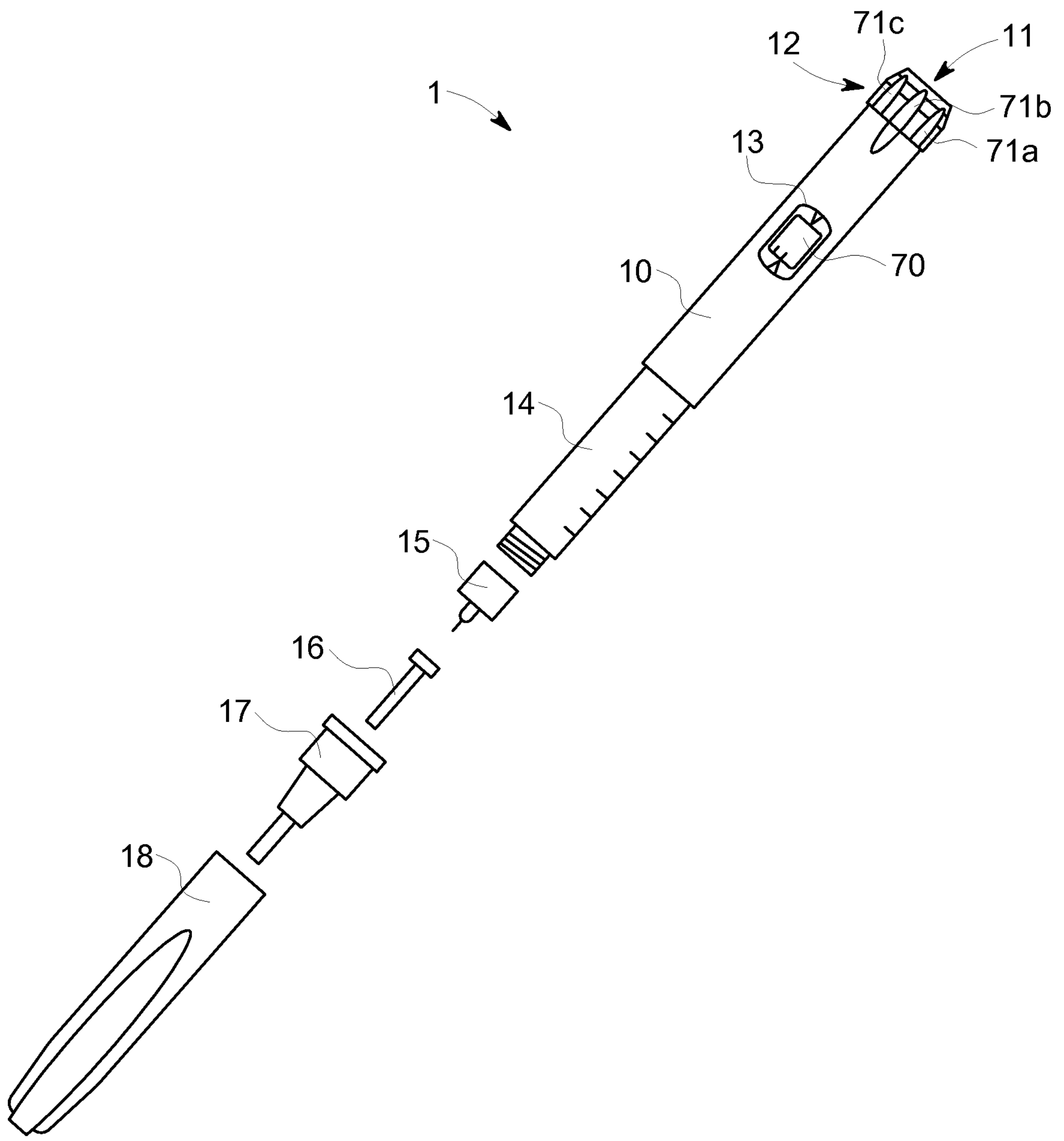
FIG. 1 shows an exploded view of an injection device for use with a data collection device according to embodiments of the present disclosure.

FIG. 1 is an exploded view of a medicament delivery device. In this example, the medicament delivery device is an injection device 1, such as an insulin injection pen. However, the embodiments of data collection apparatus disclosed herein are also compatible with other types of injection pens.

The injection device 1 of FIG. 1 is a pre-filled, disposable injection pen that comprises a housing 10 and contains an insulin container 14, to which a needle 15 can be affixed. The needle is protected by an inner needle cap 16 and an outer needle cap 17 and/or an alternative cap 18. An insulin dose to be ejected from injection device 1 can be programmed, or 'dialed in' by turning a dosage knob 12 (also referred to herein as a dose selection element 12), and a currently programmed dose is then displayed via dosage window 13, for instance in multiples of units. For example, where the injection device 1 is configured to administer human insulin, the dosage may be displayed in so-called International Units (IU), wherein one IU is the biological equivalent of about 45.5 micrograms of pure crystalline insulin (1/22 mg). Other units may be employed in injection devices for delivering analogue insulin or other medicaments. It should be noted that the selected dose may equally well be displayed differently than as shown in the dosage window 13 in FIG. 1.

The dosage window 13 may be in the form of an aperture in the housing 10, which permits a user to view a limited portion of a number sleeve 70 that is configured to move when the dosage knob 12 is turned, to provide a visual indication of a currently programmed dose. The dosage knob 12 is rotated on a helical path with respect to the housing 10 when turned during programming.

The dosage knob 12 may include one or more formations 71*a*, 71*b*, 71*c* to facilitate attachment of a data collection device and/or improve a user's grip on the dosage knob 12.

The injection device 1 may be configured so that turning the dosage knob 12 causes a mechanical click sound to provide acoustical feedback to a user. The number sleeve 70 mechanically interacts with a piston in insulin container 14. When needle 15 is stuck into a skin portion of a patient, and then injection button 11 is pushed, the insulin dose displayed in display window 13 will be ejected from injection device 1. Ejection of the insulin dose may also cause a mechanical click sound, which may be different from the sound produced when using dosage knob 12.

Injection device 1 may be used for several injection processes until either the insulin container 14 is empty or the expiration date of the medicament in the injection device 1 (e.g. 28 days after the first use) is reached.

Figure 2:
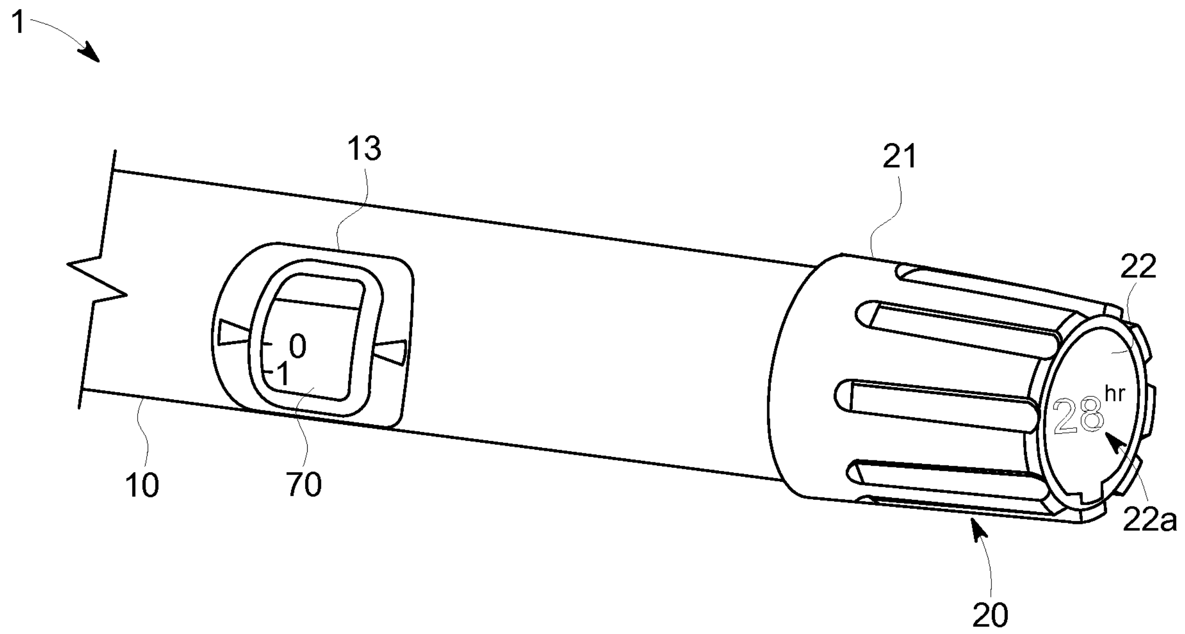
FIG. 2 shows a data collection device attached to the injection device of FIG. 1.

FIG. 2 is a perspective view of one end of the injection device 1 with a schematic illustrative example of data collection device 20 attached. The data collection device 20 includes a housing 21 and an end plate 22 with an optional display 22*a*. The data collection device 20 may take one of a number of different forms, as described below and as shown in the subsequent drawings.

Figure 3:
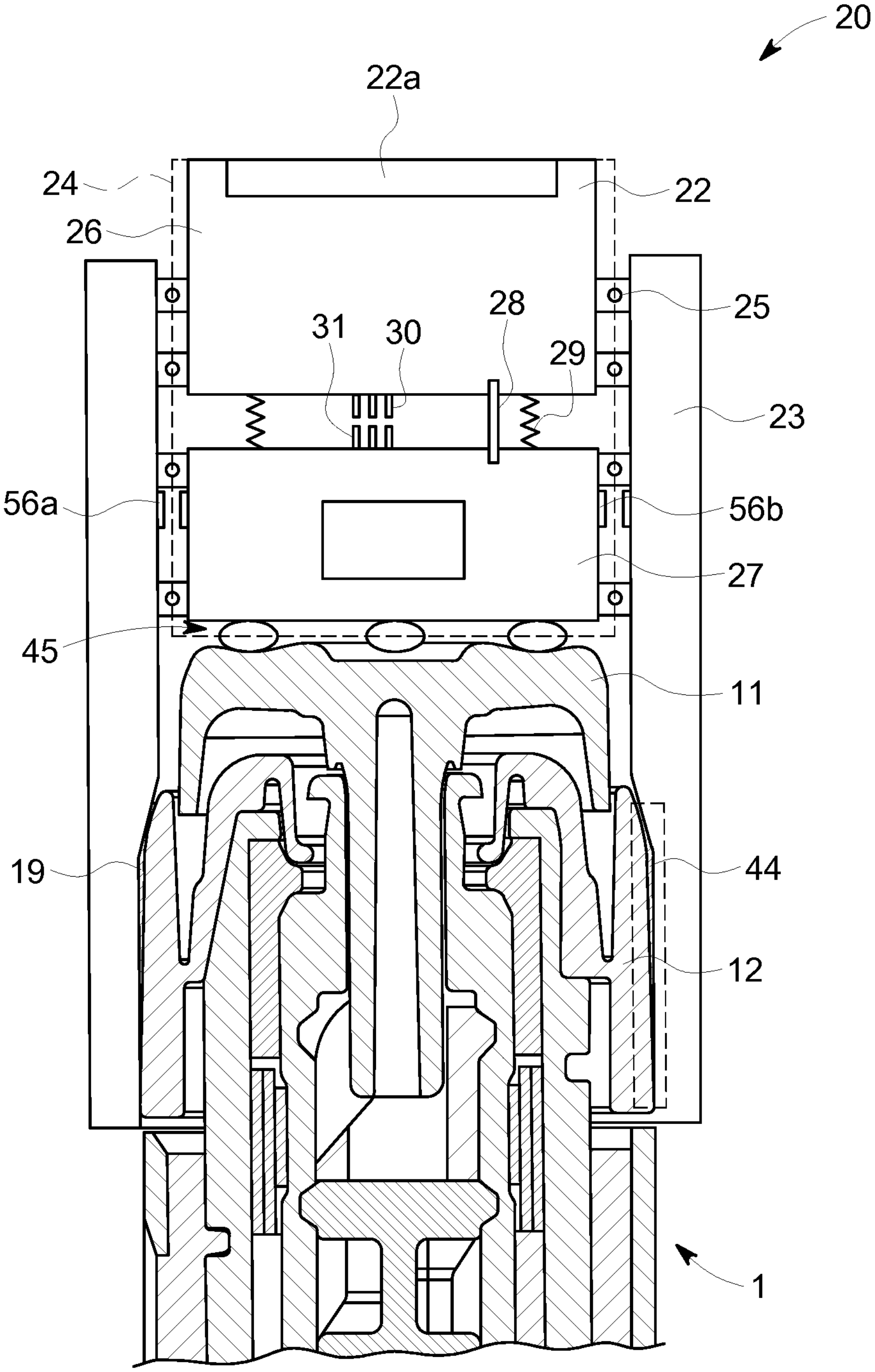
FIG. 3 is a cross-sectional view of the data collection device of FIG. 2 when attached to the injection device of FIG. 1.

FIG. 3 is a cross-sectional view of the illustrative example of data collection device 20, when attached to the injection device 1. The data collection device 20 includes a first portion 23 and a second portion 24, where the first portion 23 is capable of rotational movement relative to the second portion 24.

In this particular example, the first portion 23 is a sleeve that is positioned over the dosage knob 12. The first portion may have formations 19*a*, 19*b*, 19*c* that co-operate with the formations 71*a*, 71*b*, 71*c* on the dosage knob 12. Whether or not the formations 19*a-c* are provided on the first portion 23, the arrangement is such that, when the first portion 23 is rotated by a user during programming of the dosage, the dosage knob 12 also rotates. Also, when the dosage knob 12 rotates during expulsion of medicament, the first portion 23 also rotates.

Resilient padding, such as a foam rubber pad 44 or other deformable resilient material, may be provided within the formations 19*a-c* on the first portion 23, to allow for tolerances in the dimensions of the formations 19*a-c* on the first portion 23 and the formations 71*a*, 71*b*, 71*c* on the dosage knob 12 and/or to provide an engagement between the first portion 23 and the dosage knob 12 so that rotation of the first portion 23 causes rotation of the dosage knob 12 and vice versa.

To set a medicament dosage amount to be administered, the user may grip and rotate the first portion 23, since this will cause the dosage knob 12 of the injection device 1 to turn and, thereby, program the dosage amount.

In the particular example shown, the second portion 24 is a body located within the first portion 23, to which it is rotatably attached by bearings 25. The second portion 24 includes an outer portion 26, which includes the endplate 22 and optionally a display 22*a*. The second portion 24 also includes an inner portion 27. When the data collection device 20 is attached to the injection device 1, the inner portion 27 lies adjacent and proximate to the injection button 11. The outer portion 26 and the inner portion 27 are attached by a fixture 28 that prevents rotation relative to each other. However, in this embodiment, the outer portion 26 can be moved axially relative to the inner portion 27 and one or more resilient members, such as springs 29, may be provided to bias the outer portion 26 away from the inner portion 27. In alternative embodiments, magnets may be used to provide a repelling biasing force to bias the outer portion 26 away from the inner portion 27.

The data collection device 20 is configured to detect axial movement of the outer portion 26 relative to the inner portion 27. Movement greater than a predetermined amount may be detected using a switch 53, for instance, as is described later in the specification.

In this particular arrangement, first electrical contacts 30 are provided on the outer portion 26, while corresponding second electrical contacts 31 are provided on the inner portion 27. When a user presses the endplate 22, the outer portion 26 moves axially towards the inner portion, establishing a connection between the first and second electrical contacts 30, 31. Further pressure on the endplate 22 causes the inner portion 27 to press against, and activate, the injection button 11. The first and second electrical contacts 30, 31 provide a data connection between a processor arrangement 50 (described in more detail below) and display 22*a* when engaged.

Figure 4:
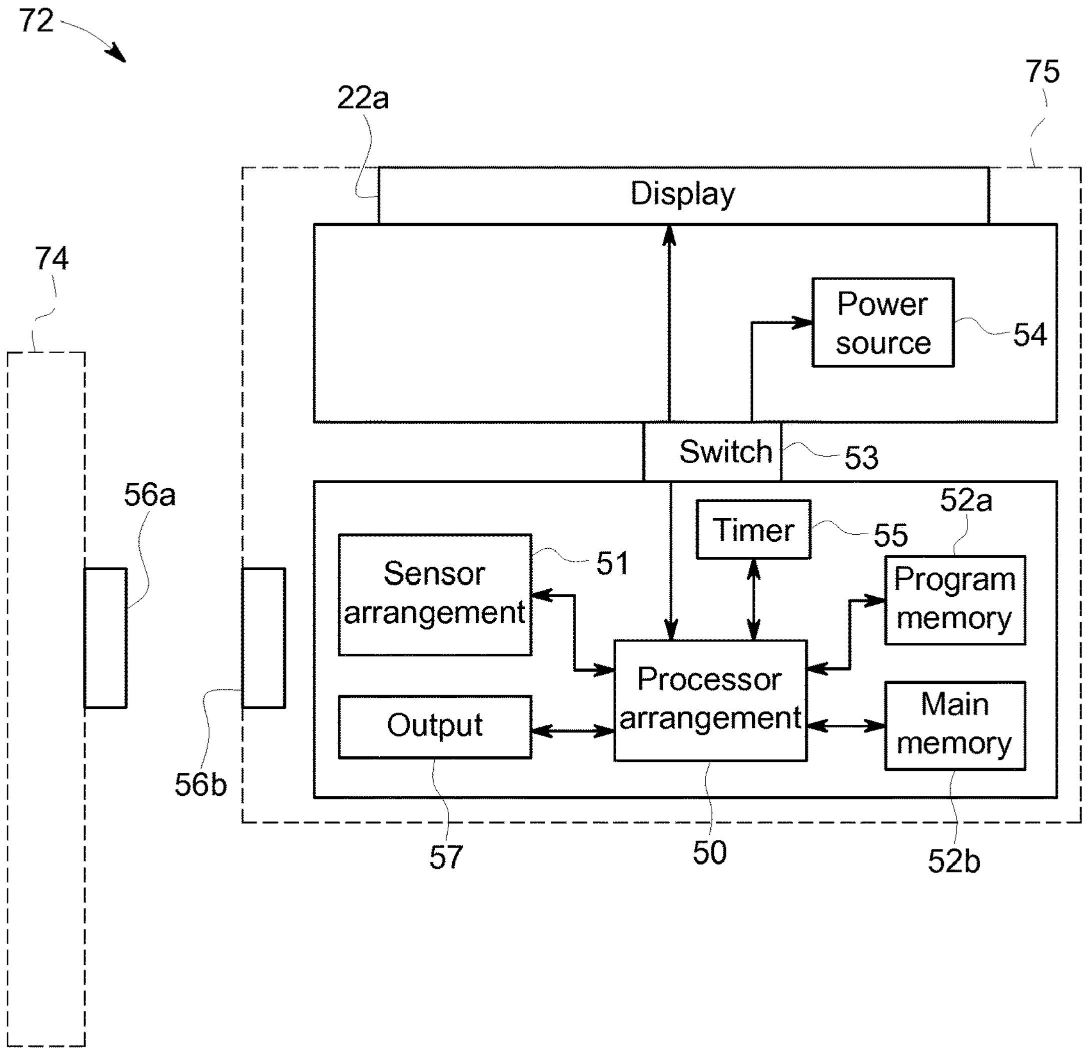
FIG. 4 shows a block diagram of components of the data collection devices of FIG. 2.

The data collection device 20 comprises a number of power and electrical/electronic components, as shown schematically in FIG. 4. These may be provided within the second portion 24, between the second portion 24 and the first portion 23, or otherwise disposed within the data collection device 20. The data collection device 20 comprises a power source 54 or battery, in the form of a coin cell in this example, and a printed circuit board (PCB). Mounted on the PCB are a number of electronic components including a communications interface, for instance a Bluetooth™ Low Energy chip or a Near Field Communications (NFC) chip. It also supports a switch 53 for detecting axial movement of the second portion 24. The PCB further supports a sensor arrangement 51, which is configured to detect rotation of the first portion 23 relative to the second portion 24. The power source 54 provides power to the electronic components of the data collection device 20.

The switch 53 is configured to be operated upon movement of at least part of the second portion 24 relative to the first portion 23. By using operation of the switch 53 to trigger powering of components of the data collection device 20, the components of the data collection device 20 will thus be powered before dose delivery commences.

Referring to FIG. 4, the data collection device 20 includes a processor arrangement 50 including one or more processors, such as a microprocessor, a Digital Signal Processor (DSP), Application Specific Integrated Circuit (ASIC), Field Programmable Gate Array (FPGA) or the like, together with memory units 52*a*, 52*b*, including program memory 52*a* and main memory 52*b*, which can store software for execution by the processor arrangement 50 and data generated during use of the data collection device such as counted pulses, derived dose size, time stamp, etc., The switch 53 connects the power source 54 to the electronic components of the device, including the sensor arrangement 51, when operated. The display 22*a* may or may not be present.

A sensor arrangement 51, comprising one or more sensors, is provided for detecting rotational movement between the first portion 23 and the second portion 24.

The resolution of the sensing arrangement 51 is determined by the design of the injection device 1. A suitable angular resolution of the sensing arrangement 51 may be determined by Equation (1):

$$\text{resolution} = \frac{360^\circ}{\text{units\_per\_rotation}} \qquad (1)$$

For instance, if one full rotation of the dosage knob 12 corresponds to a medicament dosage amount of 24 IU, then a suitable resolution for the sensing arrangement 51 would be not more than 15°.

In the exemplary embodiment shown in FIG. 3, one or more first magnets 56*a* are provided around a circumference of the inner surface of the first portion 23 and one or more second magnets 56*b* are provided around a circumference of the outer surface of the second portion 24. The sensor arrangement 51 is a transducer that varies its output due to variations in the magnetic field, based on the Hall effect, as the first portion 23 and first magnets 56*a* rotate relative to the second portion 24 and second magnets 56*b*.

Since the first portion 23 rotates with the dosage knob 12 as medicament is expelled from the injection device 1, the angle of rotation measured by the sensing arrangement 51 is proportional to the amount of medicament expelled. It is not necessary to determine a zero level or an absolute amount of medicament contained in the injection device 1. Moreover, since it is not necessary to monitor the numbers or tick marks on the number sleeve 70 displayed through the dosage window 13, the data collection device 20 may be designed so that it does not obscure the dosage window 13.

However, in other embodiments, different types of sensor may be used. For example, instead of a transducer, the sensor arrangement may include a microelectromechanical (MEMS) device or other magnetic sensor for detecting changes in a magnetic field. Another example of an sensing arrangement is an optical encoder, including a light source, such as a light emitting diode (LED) and a light detector, such as an optical transducer, that monitors changes in light reflected from an inner surface of the first portion, where the inner surface first portion has one or regions of varying reflectivity around its circumference, such as tick marks or at least one shaped reflective region.

In other embodiments, the sensing arrangement 51 may be a potentiometer. In yet other embodiments, a capacitive sensing arrangement may be used, where elements provided on the first portion 23 affect the capacitance between two plates in the sensing arrangement. In further examples, mechanical sensors, with mechanical switches and/or tracks, may be used to detect the relative rotation between the first and second portions 23, 24. Also, in embodiment, the sensor arrangement 51 may include multiple sensors of one or more types instead of a single type of sensor.

Figure 5:
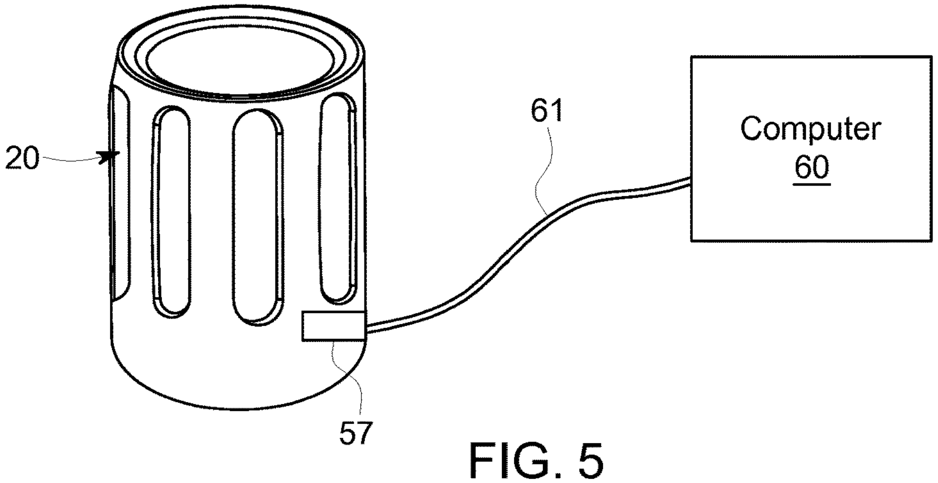
FIG. 5 shows a system in which data from the data collection device of FIG. 2 is transmitted to another device.

An output 57 is provided, which may be a wireless communications interface for communicating with another device via a wireless network such as Wi-Fi or Bluetooth®, or an interface for a wired communications link, such as a socket for receiving a Universal Series Bus (USB), mini-USB or micro-USB connector. FIG. 5 depicts an example of a system in which the data collection device 20 is connected to another device, such as a personal computer 60, via a wired connection 61 for data transfer. For example, the processor arrangement 50 may store determined delivered medicament amounts and time stamps for the injections as they are administered by the user and subsequently, transfer that stored data to the computer 60. The computer 60 maintains a treatment log and/or forwards treatment history information to a remote location, for instance, for review by a medical professional.

In another embodiment, the output 57 may be configured to transmit information using a wireless communications link and/or the processor arrangement 23 may be configured to transmit such information to the computer 40 periodically.

Figure 6A:
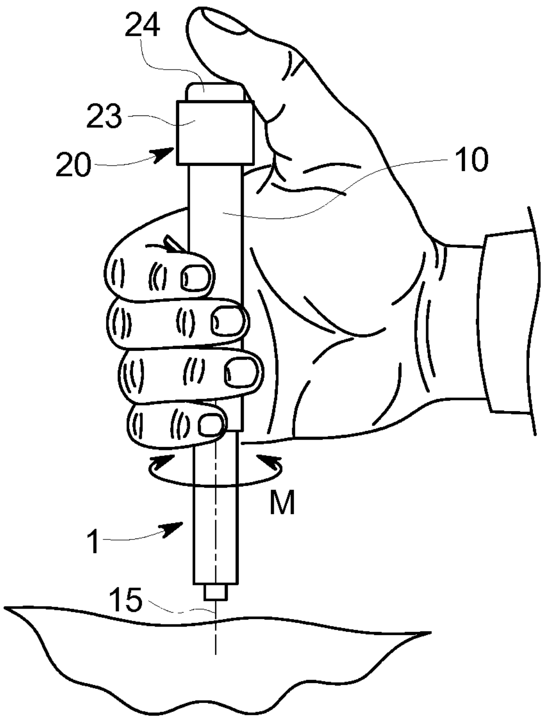
FIG. 6A shows an illustration of a first way a user may hold an injection device with attached data collection device during use.
Figure 6B:
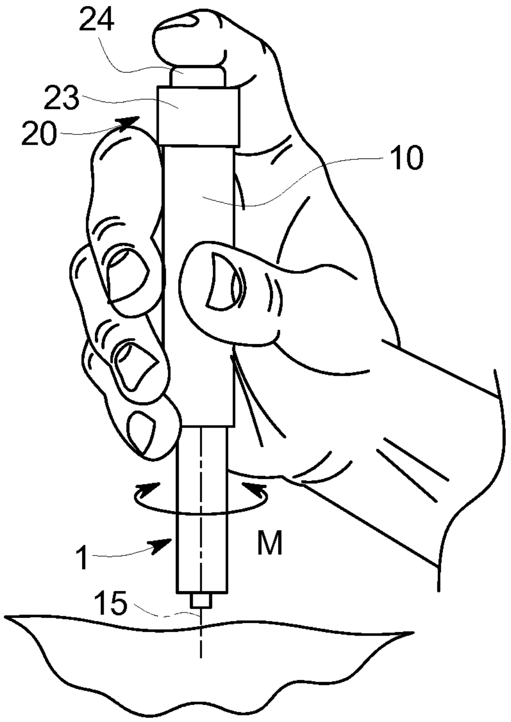
FIG. 6B shows an illustration of a second way a user may hold an injection device with attached data collection device during use.

Users generally hold such injection devices 1 in one of two ways during use, as shown in FIGS. 6A and 6B. In FIG. 6A, the user grips the injection device in the palm with all four fingers and the thumb reaches to the outer portion 26 of the second portion 24. The device is actuated by pressing the second portion 24 axially with the thumb. In FIG. 6B, the user grips the injection device housing 10 in the palm with three fingers and the thumb, and the index finger reaches to the outer portion 26 of the second portion 24. The device is actuated by pressing the second portion 24 axially with the index finger. In both configurations, it can be seen that the user's hand gripping the housing 10 and the index finger or thumb being in contact with the second portion 24 together holds the housing 10 and second portion 24 stationary relative to each other, while the first portion 23 (secured to the dosage knob 11) is able to rotate relative to the user's hand, to the housing 10 and to the second portion 24 during medicament delivery. As discussed above, it will be recalled that measurement and recording of the amount of delivered medicament is dependent on the detected relative rotation movement of the first portion 23 relative to the second portion 24.

Operation of the data collection device 20 will now be described. First, a user dials a dose into the injection device 1. This is achieved by the user rotating the first portion 23 of the data collection device 20. The rotational force is communicated to the dosage knob 12, which rotates also. During dialing, the electronics on the PCB are not powered.

The user then holds the injection device 1 and attached data collection device 20 in one hand, as shown in FIG. 6A or 6B, and injects the needle 15 into the skin of the injection site.

The user then presses the second portion 24 in order to start delivery of the dose, i.e. to cause injection. The second portion 24 moves axially in the distal direction which causes the switch 53 to be activated and therefore the electronics to be powered and thus activated. Further movement of the second portion 24 is communicated into movement of the injection button 11 in the distal direction to permit dose delivery. The dosage knob 12 begins to rotate during dose delivery and the first portion 23 thus rotates relative to the second portion 24, since the user's finger or thumb is placed on the second portion 24 holding the second portion 24 stationary relative to the user's hand and the housing 10. When the user ceases to press on the second portion 24, or when all of the dose is delivered, rotation of the first portion 23 relative to the second portion 24 ceases. The amount of rotation of the first portion 23 relative to the second portion 24 indicates the delivered dose. The amount of rotation is detected by the sensor 51, and this is used to calculate the delivered dose. The delivered dose is then stored in main memory 52*b*.

Once the user removes the distally directed force from the second portion 24, spring force from within the injection device 1 causes the injection button 11 to return the second portion 24 to the original position.

From the above description, it will be appreciated that accurate delivered dose measurement and recordal is dependent on the detected relative rotation movement of the first portion 23 relative to the second portion 24, and therefore on the first portion 23 rotating with the dosage knob 12 and the second portion 24 remaining stationary with respect to the housing 10. However, movement of the user's hand during an injection process can affect measurement accuracy. In particular, some users may loosen and tighten their grip on the housing 10 during medicament delivery. This movement, in both the grip configurations of FIGS. 6A and 6B, results in a rolling of the housing 10 within the user's palm, as shown by arrow 'M' in these figures, and does not involve movement of the index finger or thumb that is placed on the second portion 24. Therefore, housing 10 is rotated relative to the second portion 24 and so the measured relative rotation of the second portion 24 relative to the first portion 23 does not represent the actual relative rotation of the dosage knob 12 and the housing 10. Accordingly, errors may be made in the measured delivered dosage by the data collection device 20.

Figure 7:
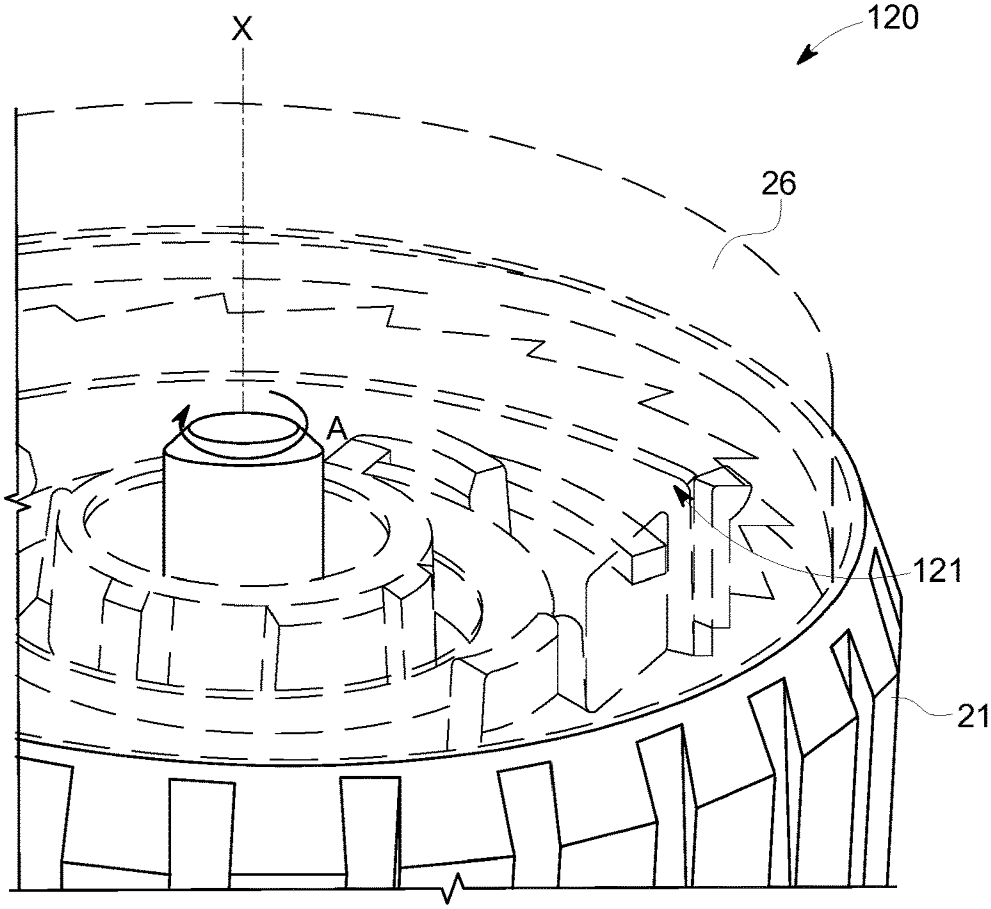
FIG. 7 shows a cut-away perspective view of a portion of a data collection device of a first embodiment.
Figure 8:
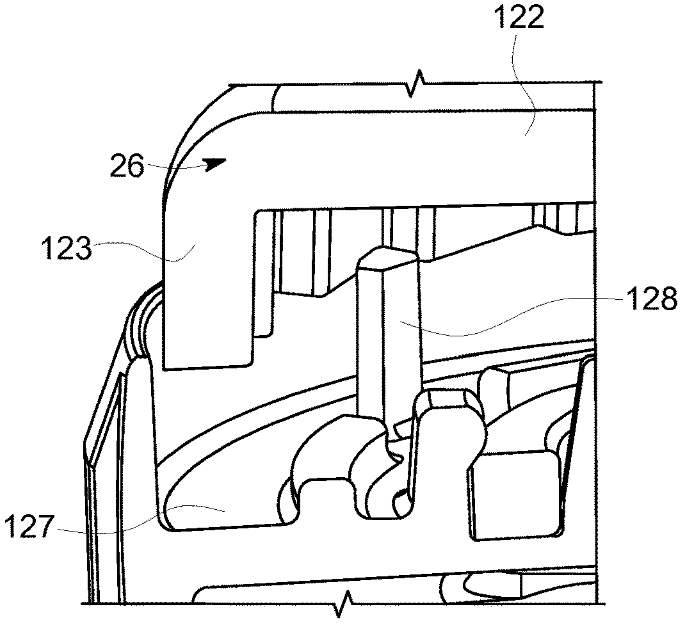
FIG. 8 shows a cross-sectional view of a portion of the data collection device of FIG. 7.
Figure 9:
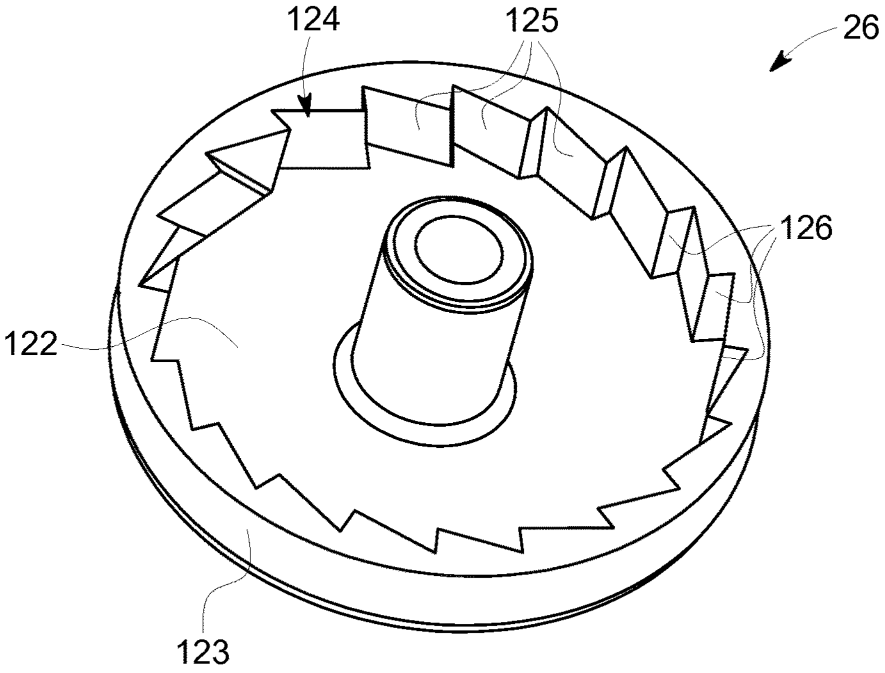
FIG. 9 shows a perspective view from below of the button of the data collection device of FIGS. 7 and 8.

In order to help towards avoiding such dosage measurement errors occurring due to user hand movement during medicament delivery, a data collection device 120 of a first embodiment includes a one-way mechanism 121, shown in FIGS. 7 to 9. Unless stated otherwise, the data collection device 120 of the first embodiment may comprise any or all features of the data collection device 20 described above. Features of the first embodiment of data collection device 120, and all subsequent embodiments described herein, in common with the data collection device 20 described above will retain the same reference numerals wherever possible.

The data collection device 120 of the first embodiment comprises a housing 21 which is analogous to the first portion 23 of the data collection device 20 described previously. The data collection device 120 also includes an outer portion or button 26 which protrudes from a proximal end of the housing 21. The button 26 is moveable both longitudinally with respect to the housing 21, and also rotationally about a common central axis X of the housing 21 and the button 26. The button 26 is coupled to the rest of a second portion or inner portion 24 of the data collection device 120 (not shown in FIGS. 7 to 9) such that longitudinal movement of the button 26 relative to the housing 21 causes corresponding longitudinal movement of the second portion 24, as described above, and with the resulting operational effect described above, with respect to the data collection device 20. The one-way mechanism 121 is configured to allow relative rotation movement between the button 26 and the housing 21 in a first rotational direction (of the button) shown by arrow 'A' in FIG. 7, but is configured to prevent relative rotational movement of the button 26 and the housing 21 in a second rotational direction opposite to the first rotational direction. Therefore, the housing 21 may rotate relative to the button 26 as occurs during medicament dose delivery as described above, but relative rotation of the button 26 and housing 21 in the opposite direction is prevented.

The button 26 has a top wall 122 and a peripheral side wall 123 that depends in the direction of the axis X distally from the perimeter of the top wall 122. The one-way mechanism 121 comprises a generally radially-inwardly facing ratchet surface 124 formed on an inside wall of the side wall 123. The ratchet surface 124 comprises a plurality of ramps 125 and steps 126 which form a generally saw-tooth configuration, which can be seen more clearly in FIG. 9.

The housing 21 includes an upper surface 127 which faces in the proximal direction and faces the button 26. A plurality of pawl pins 128 extend from the upper surface 127 in a proximal direction of the axis X towards the button 26. The pawl pins 128 engage with the ratchet surface 124 and are deflectable such that as the button 26 rotates in the first direction, the pawl pins 128 ride up the respective ramp 125 and are thereby deflected radially inwards, and then return radially outwards once they reach the respective step 126. Rotation of the button 26 in the opposite, second direction to that shown by arrow 'A', is prevent by the pawl pins 128 abutting the respective step 126. The pawl pins 128 are advantageously formed integrally with the housing 21.

The one way mechanism 121 thereby prevents the button 26, and thereby coupled second portion 24, from rotating relative to the injector device housing 10, if a user causes the injector device housing 10 to rotate by tightening and loosening their hand grip, rolling the injector device housing 10 in their hand, during a medicament injection process. Thereby, the one way mechanism 121 helps prevent errors in the measured delivered dosage by the data collection device 120.

Figure 10:
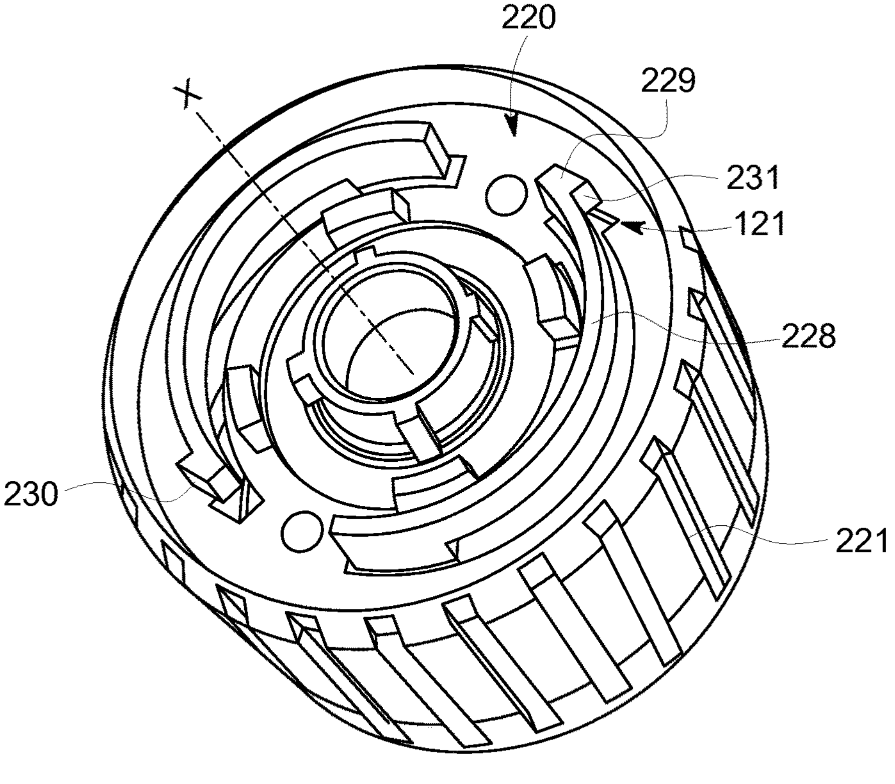
FIG. 10 shows a perspective view of a housing of a data collection device of a second embodiment with the button omitted for ease of illustration.

Referring to FIG. 10, a housing 221 of a data collection device 220 of a second embodiment is shown. The data collection device 220 of the second embodiment comprises a button 26 of the same configuration as the button 26 of the first embodiment shown in FIG. 9 (and so is not shown in FIG. 10) and is moveable both longitudinally with respect to the housing 221 and also rotationally about a central axis X of the housing 221 and the button 26. The data collection device 220 of the second embodiment also comprises a one-way mechanism 121 which is configured to allow the button 26 to rotate relative to the housing 221 in a first rotational direction, but is configured to prevent the button 26 from rotating relative to the housing 221 in a second rotational direction opposite to the first rotational direction.

A difference with the housing 221 of the second embodiment is that the upper surface 127 of the housing 21 includes a pair of arcuate pawl arms 228 having a pawl head 229 at a distal end of each. Each pawl head 229 has a ramped face 230 and a radially aligned step face 231. The pawl arms 228 are generally deflectable radially inwards with respect to the central axis X. The pawl heads 229 are biased into contact with the ratchet surface 124 of the button 26 by the resilient biasing force of the pawl arms 228. As the button 26 rotates in the first direction relative to the housing 221 (or viewed alternatively, as the housing 221 rotates about the button 226), the ramped faces 230 of the pawl heads 229 ride up the respective ramp 125 of the ratchet surface 124 and are deflected radially inwards and then return radially outwards once the pawl step face 231 reaches the respective step 126 of the ratchet surface 124. Rotation of the button 26 in the opposite, second direction is prevent by the pawl step faces 231 abutting the respective step 126 of the ratchet surface 124. The pawl arms 228 and pawl heads 229 are advantageously formed integrally with the housing 221.

Figure 11:
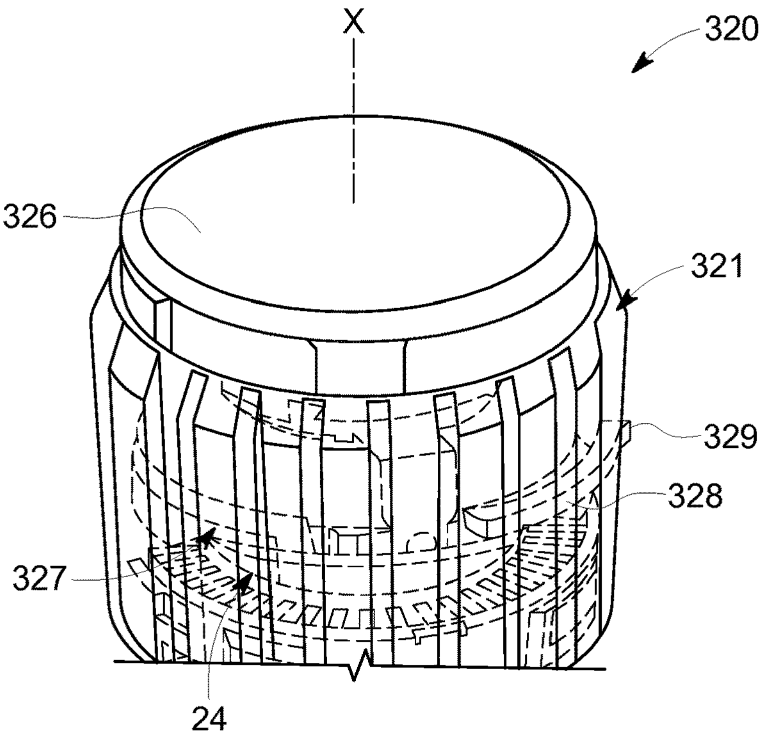
FIG. 11 shows a cut-away perspective view of a portion of a data collection device of a third embodiment.
Figure 12:
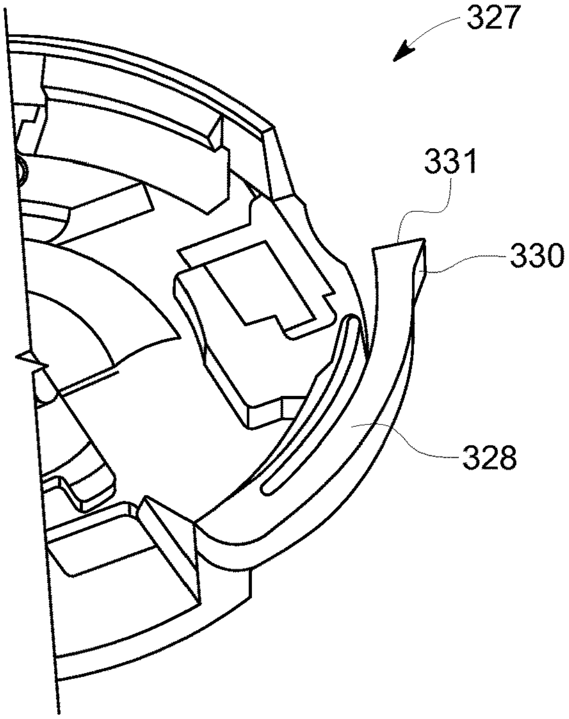
FIG. 12 shows a perspective view of a portion of a component of the data collection device of FIG. 11.

Referring to FIGS. 11 and 12 a data collection device 320 of a third embodiment is shown. The data collection device 320 of the third embodiment comprises a housing 321 and a button 326 which is moveable both longitudinally with respect to the housing 321 and also rotationally about a central axis X of the housing 321 and the button 326. The data collection device 320 of the third embodiment also comprises a one-way mechanism 121 which is configured to allow the button 326 to rotate relative to the housing 321 in a first rotational direction, but is configured to prevent the button 326 from rotating relative to the housing 321 in a second rotational direction opposite to the first rotational direction.

A difference with the data collection device 320 of the third embodiment is that it includes a button adapter 327 which is coupled to the button 326 so that the button 326 is rotationally fixed relative to the button adapter 327. The button 326 and the button adapter 327 may include cooperating locking elements (not shown) to secure the button adapter 327 to the button 326. Such cooperating locking elements may comprise elements to snap-fit the button adapter 327 to the button 326. The button adapter may be made of any suitable material and may be metallic or plastic, for example. The button adapter 327 is disposed distally within the housing 321 relative to the button 326.

The button adapter includes a pair of arcuate pawl arms 328 having a pawl head 329 at a distal end of each. Each pawl head 329 has a ramped face 330 and a radially aligned step face 331. The pawl arms 328 are generally deflectable radially inwards with respect to the central axis X. An inner wall of the housing 321 includes a generally radially-inwardly facing ratchet surface (not shown) of a similar configuration to the ratchet surface 124 formed on the inside of the side wall 123 of the button 26 of the first embodiment, and similarly comprises a plurality of ramps and steps which form a generally saw-tooth configuration.

The pawl heads 329 are biased into contact with the ratchet surface of the housing 321 by the resilient biasing force of the pawl arms 328. As the button 326 and coupled button adapter 327 rotate in the first direction relative to the housing 321 (or viewed alternatively, as the housing 321 rotates about the button 326 and the button adapter 327), the ramped faces 330 of the pawl heads 329 ride up the respective ramp of the ratchet surface and are deflected radially inwards and then return radially outwards once the pawl step face 331 reaches the respective step of the ratchet surface. Rotation of the button 326 in the opposite, second direction is prevent by the pawl step faces 331 abutting the respective step of the ratchet surface. The pawl arms 328 and pawl heads 329 are advantageously formed integrally with the button adapter 327.

Figure 13:
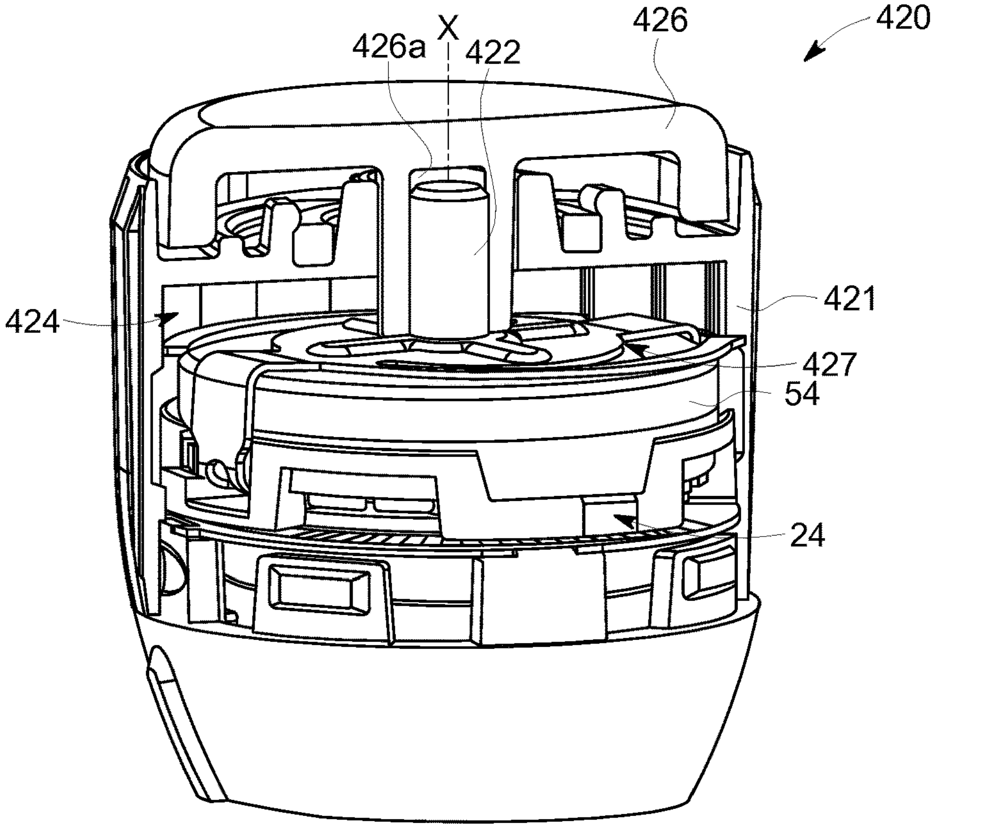
FIG. 13 shows a cross-sectional view of a data collection device of a fourth embodiment.
Figure 14:
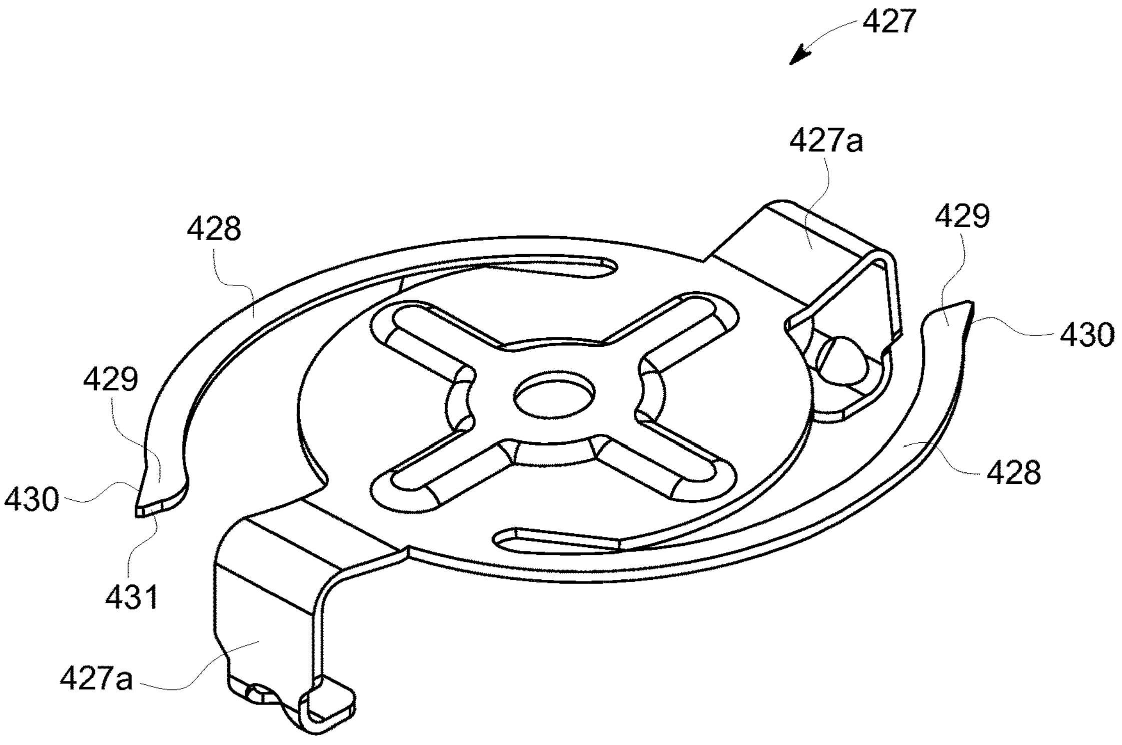
FIG. 14 shows a perspective view of a component of the data collection device of FIG. 13.

Referring to FIGS. 13 and 14 a data collection device 420 of a fourth embodiment is shown. The data collection device 420 of the fourth embodiment comprises a housing 421 and a button 426 which is moveable both longitudinally with respect to the housing 421 and also rotationally about a central axis X of the housing 421 and the button 426. The data collection device 420 of the fourth embodiment also comprises a one-way mechanism 121 which is configured to allow the button 426 to rotate relative to the housing 421 in a first rotational direction, but is configured to prevent the button 426 from rotating relative to the housing 421 in a second rotational direction opposite to the first rotational direction.

An inner wall of the housing 421 includes a generally radially-inwardly facing ratchet surface 424 comprising a plurality of ramps and steps which form a generally saw-tooth configuration. The data collection device 420 of the fourth embodiment includes a battery contact plate 427 which is associated with the power and electrical/electronic components as part of the second portion 24 which is disposed within, and rotatable relative to, the housing 421. The battery contact plate 427 is configured to retain a battery, in this embodiment, a coin cell 54, by means of curved retaining arms 427*a*. The button 426 is rotationally fixed relative to the battery contact plate 427 and the second portion 24 containing power and control electronics. The button 426 and the battery contact plate 427 may include cooperating locking elements to secure the battery contact plate 427 to the button 426. In the embodiment shown, a mounting post 422 extends from the collection of electrical/electronic components of the second portion 24 and the post 422 extends through a central aperture in the battery contact plate 427 and is secured within a central recess 426*a* of the button 426. The battery contact plate 427 is disposed distally within the housing 421 relative to the button 426.

The battery contact plate 427 includes a pair of arcuate spring or pawl arms 428 having a pawl head 429 at a distal end of each. Each pawl head 429 has a ramped face 430 and a radially aligned step face 431. The pawl arms 428 are generally deflectable radially inwards with respect to the central axis X due to the resilience of the material from which the battery contact plate 427 is made. This may be metallic and may be steel.

The pawl heads 429 are biased into contact with the ratchet surface 424 of the housing 421 by the resilient biasing force of the pawl arms 428. As the button 426 and connected battery contact plate 427 rotate in the first direction relative to the housing 421 (or viewed alternatively, as the housing 421 rotates about the button 426, battery contact plate 427 and second portion 24), the ramped faces 430 of the pawl heads 429 ride up the respective ramp of the ratchet surface 424 and are deflected radially inwards and then return radially outwards once the pawl step face 431 reaches the respective step of the ratchet surface 424. Rotation of the button 426/battery contact plate 427/second portion 24 relative to the housing 421 in the opposite, second direction is prevent by the pawl step faces 431 abutting the respective step of the ratchet surface 424. The pawl arms 428 and pawl heads 429 are advantageously formed integrally with the battery contact plate 427. An advantageous benefit of such a configuration is that the pawl arms 428/pawl heads 429 of the one-way mechanism 121 are integrally formed with a component of the electrical components, and which reduced the number of additional component parts of the device 420, helping towards reducing part count, cost and complexity.

Figure 15:
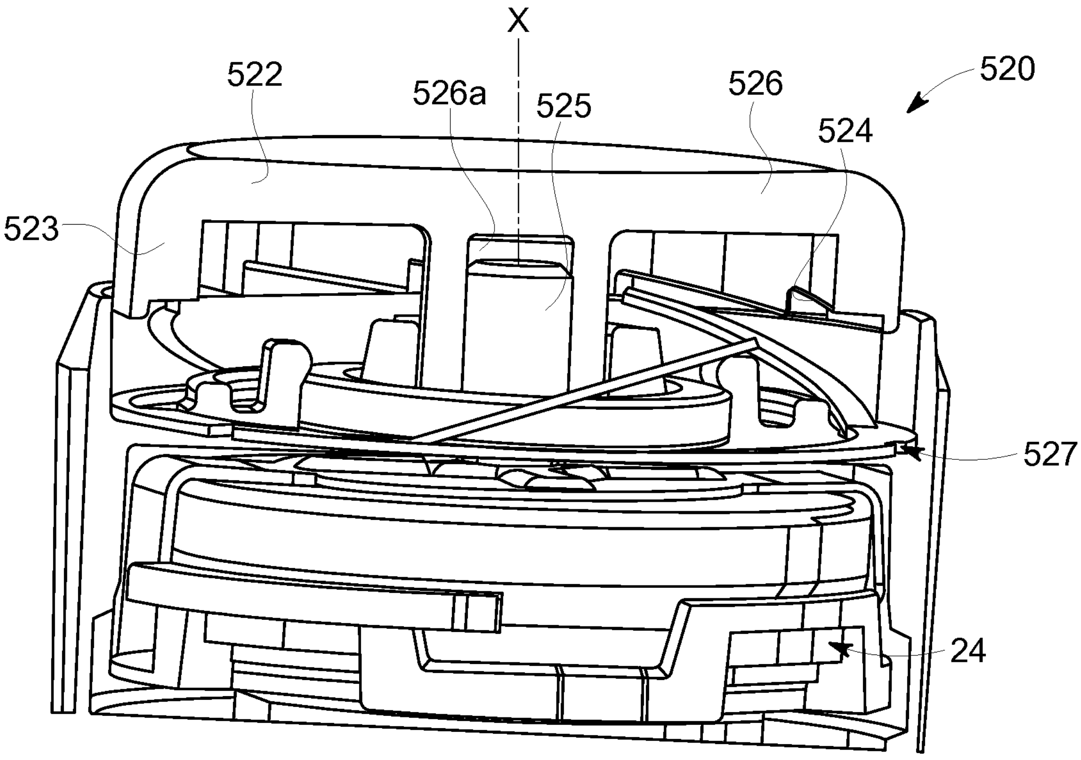
FIG. 15 shows a cross-sectional view of a data collection device of a fifth embodiment.
Figure 16:
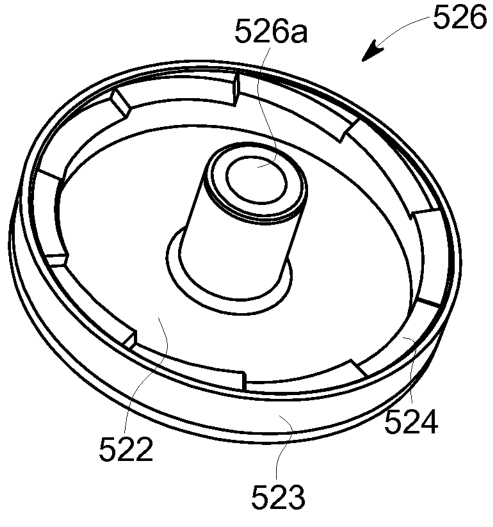
FIG. 16 shows a perspective view from below of the button of the data collection device of FIG. 15.
Figure 17:
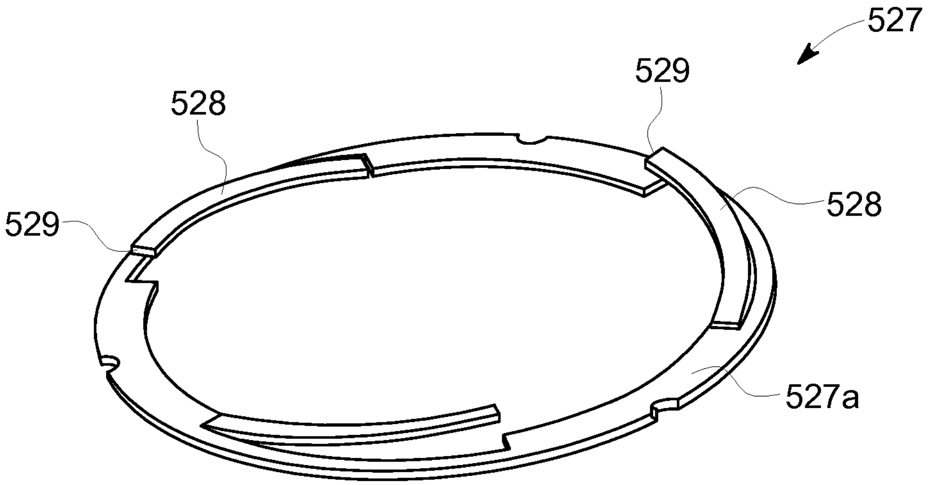
FIG. 17 shows a perspective view of a component of the data collection device of FIG. 15.

Referring to FIGS. 15 to 17, a data collection device 520 of a fifth embodiment is shown. The data collection device 520 of the fifth embodiment comprises a housing 521 and a button 526 which is moveable both longitudinally with respect to the housing 521 and also rotationally about a central axis X of the housing 521 and the button 526. The data collection device 520 of the fifth embodiment also comprises a one-way mechanism 121 which is configured to allow rotation movement of the button 526 relative to the housing 521 in a first rotational direction, but is configured to prevent rotational movement of the button 526 relative to the housing 521 in a second rotational direction opposite to the first rotational direction.

The button 526 includes a top wall 522 and a peripheral side wall 523 that depends in the direction of the axis X distally from the perimeter of the top wall 522. A generally axially-facing ratchet surface 524 is formed on an axially distal end face of the side wall 523 and comprises a plurality of ramps and steps which form a generally saw-tooth configuration.

The data collection device 520 of the fifth embodiment includes a latch ring 527 which is disposed within the housing 521 between the button 526 and the power and electrical/electronic components of the second portion 24. The button 526 is rotationally fixed relative to the power and electrical/electronic components of the second portion 24, and may include cooperating locking elements to secure the button 526 to the electrical/electronic components of the second portion 24. In the embodiment shown, a mounting post 525 extends from the collection of electrical/electronic components of the second portion 24, and the post 525 is secured within a central recess 526*a* of the button 526. The button 526 is moveable from a deactivated position, in which it partially extends from the housing 521, to an activated position, in which it is further received within the housing 521 than in the deactivated position. Movement of the button 526 axially in the distal direction from the deactivated position to the activated position causes the attached post 525 to push a portion of the electrical components in the second portion 24 in the axially distal direction to make first and second electrical contacts 30, 31 connect, or switch 53 closed, to power up the data collection device 520 for operation as described previously.

The latch ring 527 comprises a circular body 527*a* and a plurality of spring or pawl arms 528 which have remote ends 529. Each pawl arm 528 extends away from the circular body 527*a* in an axial proximal direction. The pawl arms 528 are generally deflectable axially distally toward the circular body 527*a* due to the resilience of the material from which the latch ring 527 is made. This may be metallic and may be steel, or may be a plastic material. The circular body 527*a* of the latch ring 527 is fixed to the housing 521 and thereby rotates together with the housing 521. Therefore, the button 526 is rotatable relative to the latch ring 527.

The ends 529 of the pawl arms 528 are biased into contact with the ratchet surface 524 of the button 526 by the resilient biasing force of the pawl arms 528. The pawl arms 528 therefore also bias the button 526 in an axially proximal direction towards the deactivated position. As the button 526 rotates relative to the housing 521 in the first direction (or viewed alternatively, as the housing 521 rotates about the button 526 and other components within the second portion 24 about which the housing 521 rotates), the ends 529 of the pawl arms 528 ride up the respective ramp of the ratchet surface 524 and are deflected axially distally and then return axially proximally once the ends 529 reach the respective step of the ratchet surface 524. Rotation of the button 526/second portion 24 relative to the housing 521 in the opposite, second direction is prevent by the ends 529 of the pawl arms 528 abutting the respective step of the ratchet surface 524. The pawl arms 528 are advantageously formed integrally with the latch ring body 527*a*. It will be appreciated that a further advantageous feature of the data collection device 520 of the fifth embodiment is that the pawl arms 528 of the latch ring 527 act to bias the button 526 into the deactivated position. Therefore, after use, once a user has released their finger or thumb from the button 526, the button is pushed back into the deactivated position which causes the attached post 525 to pull the portion of the electrical components in the second portion 24 in the axially proximal direction to make first and second electrical contacts 30, 31 disconnect, or switch 53 open, to power down the data collection device 520. This may help preserve battery life by ensuring the data collection device 520 does not inadvertently remain switched on after use. The may also help towards avoiding false dose recording by any accidental movement of the housing 521 relative to the button 526/second portion 24 after the medicament delivery has stopped. This is advantageous in this fifth embodiment as the function of biasing the button 526 into the deactivated position is performed by a common component of the one-way mechanism 121, thereby reducing the number of component parts required, simplifying device design and manufacture, and reducing cost. However, it will be appreciated that the first to fourth embodiments of data collection devices 120, 220, 320, 420 described previously may additionally be provided with a button biasing element, such as a spring element or magnets, to bias the respective button axially proximally to achieve the same advantageous effect of deactivating the device after use as described above. In all such variations of the previously-described embodiments therefore, it is envisaged that the button may be moveable from a deactivated position, in which it partially extends from the housing, to an activated position, in which it is further received within the housing than in the deactivated position. Movement of the button axially in the distal direction from the deactivated position to the activated position would move a portion of the electrical components in the second portion 24 in the axially distal direction to make first and second electrical contacts 30, 31 connect, or switch 53 closed, to power up the respective data collection device for operation as described previously.

Figure 18:
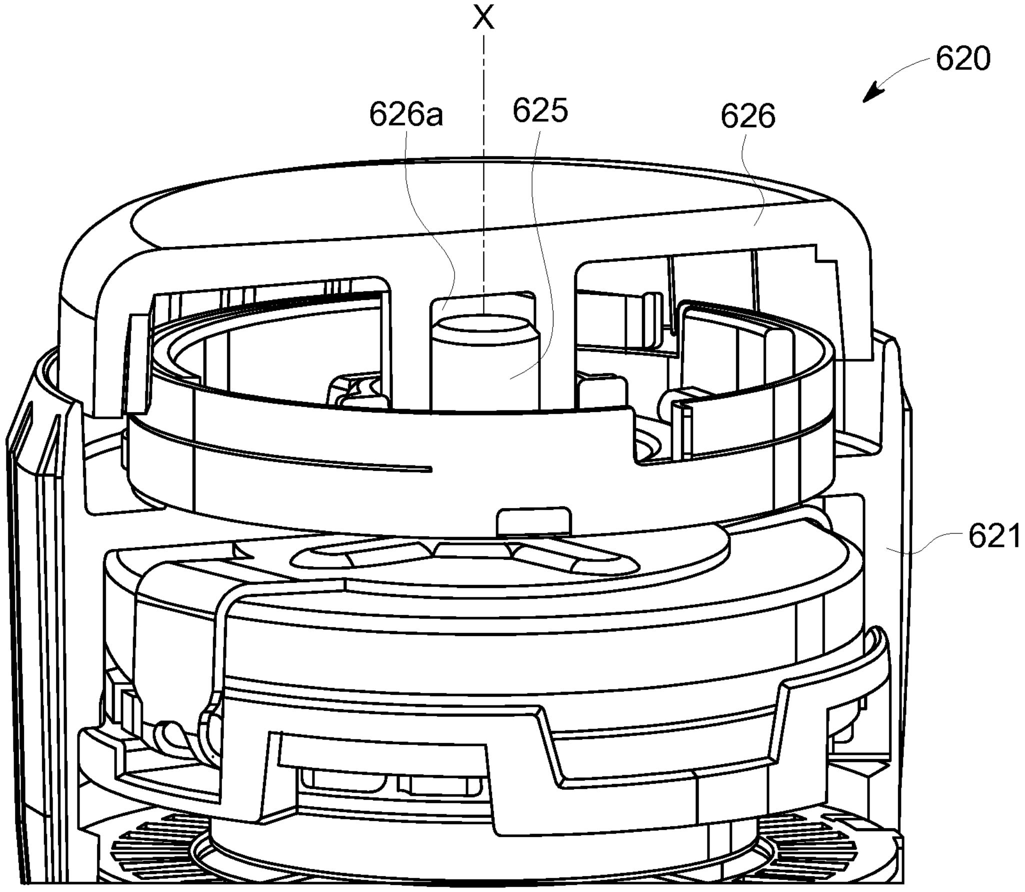
FIG. 18 shows a cross-sectional view of a data collection device of a sixth embodiment.
Figure 19:
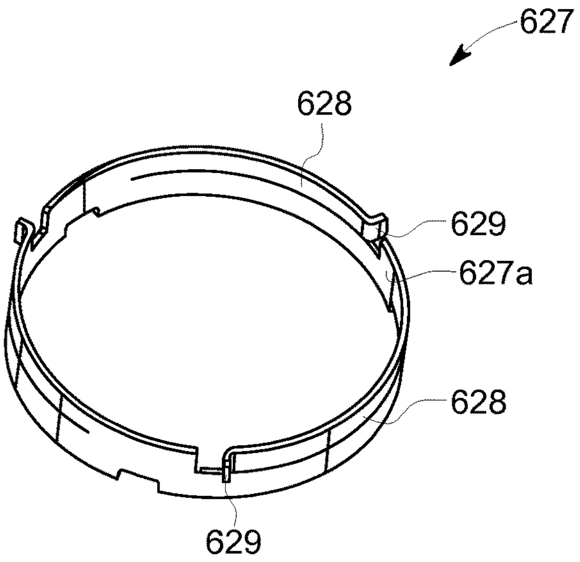
FIG. 19 shows a perspective view of a component of the data collection device of FIG. 18.

Referring to FIGS. 18 and 19, a data collection device 620 of a sixth embodiment is shown, and is similar to the data collection device 520 of the fifth embodiment, comprising a housing 621 and a button 626 which is moveable both longitudinally with respect to the housing 621 and also rotationally about a central axis X of the housing 621 and the button 626. The data collection device 620 of the sixth embodiment also comprises a one-way mechanism 121 which is configured to allow rotation movement of the button 626 relative to the housing 621 in a first rotational direction, but is configured to prevent rotational movement of the button 626 relative to the housing 621 in a second rotational direction opposite to the first rotational direction.

The button 626 is similar to the button 26 shown in FIG. 9, and includes generally radially inwardly-facing ratchet surface 624 comprising a plurality of ramps and steps which form a generally saw-tooth configuration.

The data collection device 620 of the sixth embodiment includes a latch ring 627 which is disposed within the housing 621 between the button 626 and the power and electrical/electronic components of the second portion 24. The button 626 is rotationally fixed relative to the power and electrical/electronic components of the second portion 24, and may include cooperating locking elements to secure the button 626 to the electrical/electronic components of the second portion 24. In the embodiment shown, a mounting post 625 extends from the collection of electrical/electronic components of the second portion 24, and the post 625 is secured within a central recess 626*a* of the button 626. The button 626 is moveable from a deactivated position, in which it partially extends from the housing 621, to an activated position, in which it is further received within the housing 621 than in the deactivated position. Movement of the button 626 axially in the distal direction from the deactivated position to the activated position causes the attached post 625 to push a portion of the electrical components in the second portion 24 in the axially distal direction to make first and second electrical contacts 30, 31 connect, or switch 53 closed, to power up the data collection device 620 for operation as described previously.

A difference over the data collection device 520 of the fifth embodiment, is in the configuration of the latch ring 627. Instead of axially-extending pawl arms, the latch ring 627 of the sixth embodiment comprises a circular body 627*a* and a plurality of spring or pawl arms 628 which are deflectable in a generally radial direction relative to the axis X and circular body 627*a*. The pawl arms 628 are deflectable from a relaxed position (as shown in FIG. 19) in which they are generally aligned in an axial direction with the circular body 627*a*, to a deflected position, in which they are generally deflected further radially inwardly relative to axis X than in the relaxed position. The latch ring 627 may be metallic and may be steel, or may be a plastic material. The circular body 627*a* of the latch ring 627 is fixed to the housing 621 and thereby rotates together with the housing 621. Therefore, the button 626 is rotatable relative to the latch ring 627.

The pawl arms 628 have radially extending end portions 629 which are in contact with the ratchet surface 624 of the button 626, and may be biased into contact by the resilient biasing force of the pawl arms 628. As the button 626 rotates relative to the housing 621 in the first direction (or viewed alternatively, as the housing 621 rotates about the button 626 and other components within the second portion 24 about which the housing 621 rotates), the end portions 629 of the pawl arms 628 ride up the respective ramp of the ratchet surface 624 and are deflected radially inwards and then return radially outwards once the end portions 629 reach the respective step of the ratchet surface 624. Rotation of the button 626/second portion 24 relative to the housing 621 in the opposite, second direction is prevent by the end portions 629 of the pawl arms 628 abutting the respective step of the ratchet surface 624. The pawl arms 628 are advantageously formed integrally with the latch ring body 627*a*. The data collection device 620 of the sixth embodiment may additionally be provided with a button biasing element (not shown), such as a spring element, to bias the button 626 axially proximally into the deactivated position to achieve the same advantageous effect of deactivating the device after use as described above.

It is will be appreciated that variations of the fifth and sixth embodiments of data collection devices 520, 620 described above are anticipated, in which the latch rings 527, 627 may alternatively be fixedly secured to the respective button 526, 626, and the ratchet surface 524, 624 may be formed instead on a portion of the housing 521, 621 which is rotatable relative to the respective button 526, 626.

Figure 20:
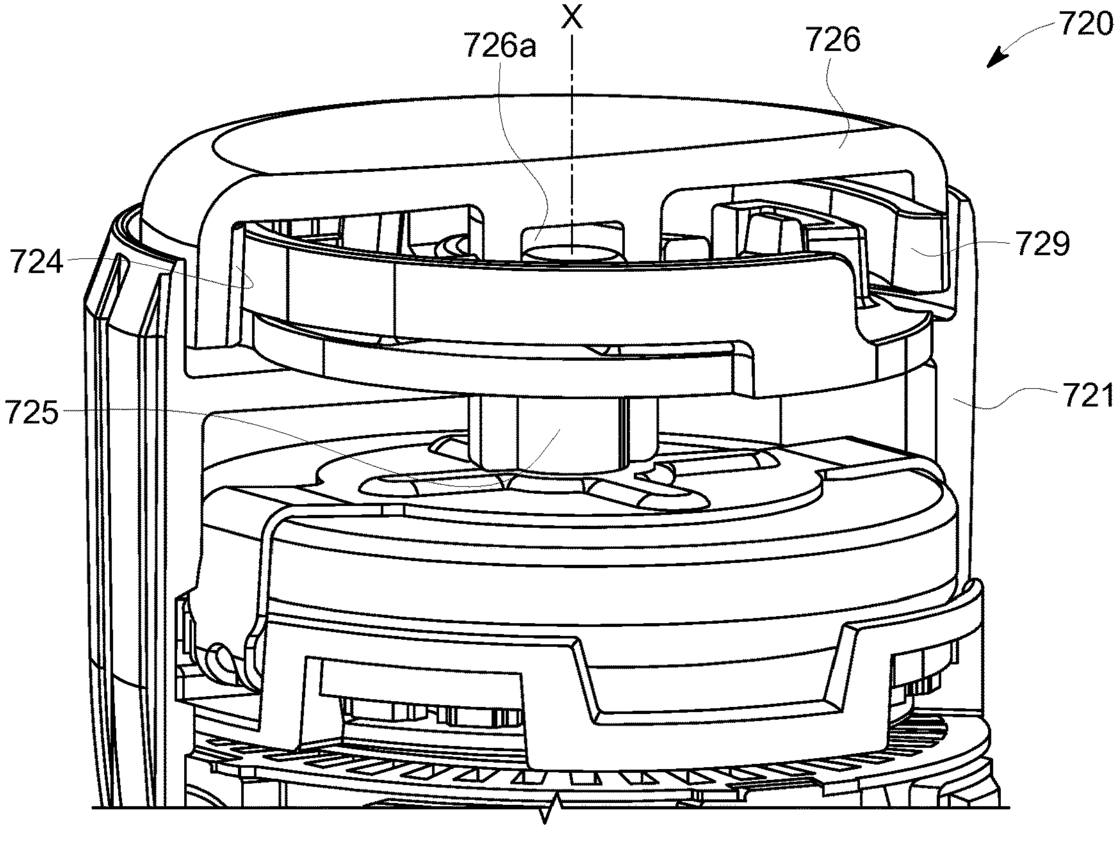
FIG. 20 shows a cross-sectional view of a data collection device of a seventh embodiment.
Figure 21:
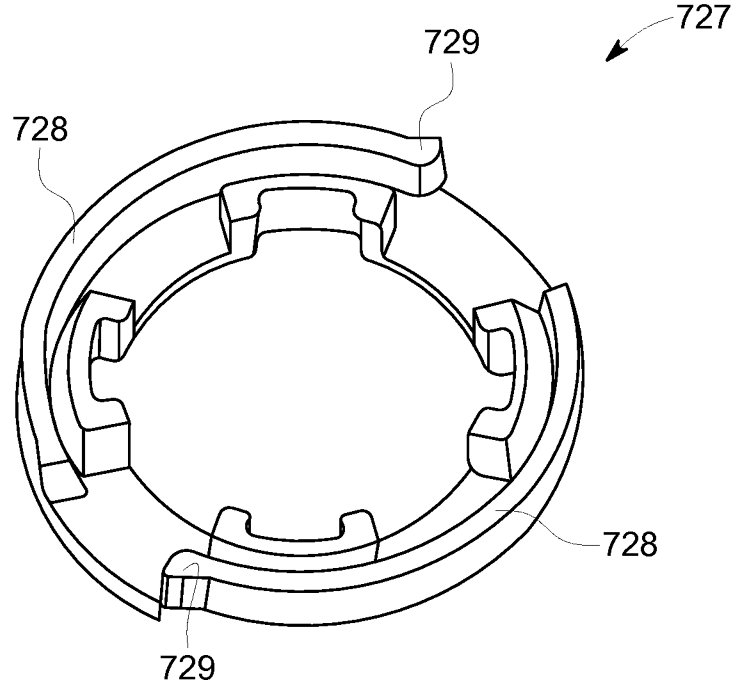
FIG. 21 shows a perspective view of a component of the data collection device of FIG. 20.

Referring to FIGS. 20 and 21, a data collection device 720 of a seventh embodiment is shown, and comprises a housing 721 and a button 726 which is moveable both longitudinally with respect to the housing 721 and also rotationally about a central axis X of the housing 721 and the button 726. The data collection device 720 of the seventh embodiment also comprises a one-way mechanism 121 which is configured to allow rotation movement of the button 726 relative to the housing 721 in a first rotational direction, but is configured to prevent rotational movement of the button 726 relative to the housing 721 in a second rotational direction opposite to the first rotational direction.

The button 726 is similar to the button 26 shown in FIG. 9, and includes generally radially inwardly-facing ratchet surface 724 comprising a plurality of ramps and steps which form a generally saw-tooth configuration.

The data collection device 720 of the seventh embodiment includes a button adapter 727 which is disposed within the housing 721 between the button 726 and the power and electrical/electronic components of the second portion 24. The button 726 may be rotationally fixed relative to the power and electrical/electronic components of the second portion 24, and may include cooperating locking elements to secure the button 726 to the electrical/electronic components of the second portion 24. In the embodiment shown, a mounting post 725 extends from the collection of electrical/electronic components of the second portion 24, and the post 725 is secured within a central recess 726*a* of the button 726. The button 726 is moveable from a deactivated position (not shown), in which it partially extends from the housing 721, to an activated position (as shown in FIG. 20), in which it is further received within the housing 721 than in the deactivated position. Movement of the button 726 axially in the distal direction from the deactivated position to the activated position causes the attached post 725 to push a portion of the electrical components in the second portion 24 in the axially distal direction to make first and second electrical contacts 30, 31 connect, or switch 53 closed, to power up the data collection device 720 for operation as described previously.

A difference with the data collection device 720 of the seventh embodiment is the configuration and operation of the button adapter 727 with the button 726. Broadly speaking, the one-way mechanism 121 is configurable between a disengaged position, in which the button 726 is freely-rotatable relative to the housing 721, and an engaged in which rotational movement of the button 726 relative to the housing 721 is permitted only in the first direction as described above. The one-way mechanism 121 is configurable from the disengaged position to the engaged position by movement of the button 726 from the deactivated position towards the activated position.

The button adapter 727 comprises a circular body 727*a* and a plurality of pawl arms 728 having pawl heads 729 configured for engagement with the ratchet surface 724 of the button 726. The pawl heads 729 may be deflectable radially inwards on the pawl arms 728, or may be formed of a resilient material to elastically deform radially inwardly without movement of the respective pawl arm 728. The button adapter 727 may be metallic and may be steel, or may be a plastic material. In the exemplary embodiment shown in FIGS. 20 and 21, the button adapter 727 is fixed to the housing 721 and thereby rotates together with the housing 721. In the deactivated position of the button 726, the button 726 is axially spaced from the button adapter 727 so that the pawl heads 729 are out of engagement with the ratchet surface 724. When the button 726 is moved towards the activated position, the pawl heads 729 are moved into engagement with the ratchet surface 724.

When the button 726 is in the activated position, and so the one-way mechanism 121 is in the engaged position, as the button 726 rotates relative to the housing 721 in the first direction (or viewed alternatively, as the housing 721 rotates about the button 726 and other components within the second portion 24 about which the housing 721 rotates), the pawl heads 729 ride up the respective ramp of the ratchet surface 724 and are deflected or deformed radially inwards and then return radially outwards once the pawl heads 729 reach the respective step of the ratchet surface 724. Rotation of the button 726/second portion 24 relative to the housing 721 in the opposite, second direction is prevent by the pawl heads 729 abutting the respective step of the ratchet surface 724. The pawl arms 728 and pawl heads 729 are advantageously formed integrally with the button adapter body 727*a*. The data collection device 720 may additionally be provided with a button biasing element (not shown), such as a spring element, to bias the button 726 axially proximally towards the deactivated position to achieve the same advantageous effect of deactivating the device after use as described above.

An advantage of the configuration of one-way mechanism 121 of the seventh embodiment 720 is that the mechanism is only engaged when the device is in the activated position. Therefore, the button 726 is able to "free-wheel" relative to the housing 721 only when the button 726 is in the deactivated position and so the data collection device 720 is powered off and not in use, and so unable to record any false dosage measurements that would otherwise occur from free-wheeling of the button 726 relative to the housing 721. It is an intended variant of all of the previously described embodiments that the one-way mechanism of each may be configurable as described above, namely that movement of the respective button from the deactivated portion to the activated position also causes the respective one way mechanism to move from a disengaged, free-wheel configuration, to an engaged configuration in which the previously-described rotational one-way movement of the button relative to the housing is effected.

In the above-described seventh embodiment 720, the button adapter 727 is fixedly secured to the housing 721, that is, it is unable to move axially or rotationally relative to the housing 721. However, in an intended variant of the seventh embodiment 720, the button adapter 727 may be axially secured to the button 726 so that it cannot move axially relative to the button 726. The button adapter 727 may only be able to move in one direction relative to the button 726 but prevented from relative rotation in the opposite direction relative to the button. In such an embodiment, the button adapter 727 may include one or more locking elements (not shown) configured to engage with one or more corresponding locking elements (not shown) on the housing 721. As the button 726 and axially-secured button adapter 727 are moved in an axially distal direction into the housing 721, the cooperating locking elements on the button adapter 727 and housing 721 engage to prevent relative rotational movement of the button adapter 727 relative to the housing 721. Thereafter, operation of this variant of the seventh embodiment would be as described previously for the seventh embodiment.

A further intended variant of the seventh embodiment 720 is envisaged, in which the button adapter 727 may be both axially and rotationally secured to the button 726 so that it cannot move axially or rotationally relative to the button 726. In such a further variant, the button 726 would not include a ratchet surface 724, but instead the ratchet surface 724 would be provided on an inside wall of the housing 721. In the deactivated position of the button 726, the pawl heads 729 would be axially spaced and out of engagement with the ratchet surface 724 on the housing 721. As the button 726 and the button adapter 727 are moved in an axial distal direction into the housing 721 into the activated position, the pawl heads 729 on the button adapter 727 would come into cooperating engagement with the ratchet surface 724 of the housing 721 to allow relative rotational movement of the button 726 and button adapter 727 relative to the housing 721 only in one rotational direction. Thereafter, operation of this further variant of the seventh embodiment would be as described previously for the seventh embodiment.

In variants intended to the above-described embodiments within the scope of the present disclosure, it is intended that the one-way mechanism may not include ratchet and follower element, and may instead comprise other configurations of cooperating features to effect the one-way rotational movement of the button relative to the housing as described above. Such alternative one-way mechanisms may, for example, comprise a freewheel or overrunning clutch arrangement, for example comprising bearings or rotary cylinders acting against a relatively rotating cylindrical surface.

In variants of the embodiments described herein, it is intended that the respective button may be a top part of second portion and integrally formed with second portion, analogous to the schematic view of FIG. 3.

In all embodiments described herein comprising a ratchet surface formed on one component and a cooperating follower element or other feature on another component configured to engage with the ratchet surface to allow relative rotational movement of the one component relative to the another component, it is intended that variants of such embodiments may be provided in which the ratchet surface and the follower element or other feature configured to engage the ratchet surface may be reversed—that is, provided on the other of the components respectively.

A power switch may be provided, which may comprise the first and second electrical contacts, 31, or the switch 53, such that the power switch responds to pressure applied to the second portion 24 by powering the data collection device 20 on or off, so that power may conserved when the injection device 1 is not being used. In such an arrangement, when the data collection device 20 is powered on again, the processor arrangement 50 may control the display 22*a* to show the determined medicament dose information 22*a*, to aid the memory of the user, and/or an elapsed time since the determined medicament dose was delivered. For example, the processor arrangement 23 may cause the display 22*a* to switch periodically between displaying the most recent determined medicament dosage information and the elapsed time.

The power source 54 may be a battery. In some embodiments, the endplate 22 may include a solar panel to recharge a rechargeable battery. The power source may be a coin cell, or multiple coin cells arranged in series or parallel. In another embodiment, the power source 54 may be a piezo-electric generator, which generates power when the endplate 22 is pressed by the user, potentially avoiding the need for a battery.

A timer 55 is also provided. In addition to, or instead of, switching the data collection device 20 on and off, the switch 53 or the first and second electrical contacts 30, 31 may be arranged to trigger the timer 55 when engaged and/or disengaged. For example, if the timer 55 is triggered on both engagement or disengagement of the first and second electrical contacts 30, 31, or both operation and ceasing of operation of the switch 53, then the processor arrangement 50 may use the output from the timer to determine a length of time during which the injection button 11 was pressed, for example to determine the duration of an injection.

Alternatively, or additionally, the processor arrangement 50 may use the timer 55 to monitor a length of time that has elapsed since an injection was completed, as indicated by a time of disengagement of the first and second electrical contacts 30, 31 or ceasing of operation of the switch 53. Optionally, the elapsed time may be shown on the display 22*a*, as depicted in FIG. 2. Also optionally, when the first and second contacts 30, 31 are next engaged or when the switch 53 is next operated, the processor arrangement 50 may compare the elapsed time with a predetermined threshold, to determine whether a user may be attempting to administer another injection too soon after a previous injection and, if so, generate an alert such as an audible signal and/or a warning message on the display 22*a*. On the other hand, if the elapsed time is very short, it may indicate that the user is administering a medicament amount as a "split dose", and the processor arrangement 50 may store information indicating that a dosage was delivered in that manner.

Another optional purpose for monitoring the elapsed time by the processor arrangement 50 is to determine when the elapsed time has passed a predetermined threshold, suggesting that the user might have forgotten to administer another injection and, if so, generate an alert.

While the embodiments above have been described in relation to collecting data from an insulin injector pen, it is noted that embodiments of the present disclosure may be used for other purposes, such as monitoring of injections of other medicaments.

The injection device 1 is configured to inject or infuse a medicament into a patient. For example, delivery could be sub-cutaneous, intra-muscular, or intravenous. Delivery could be needleless. The injection device 1 could be operated by a patient or care-giver, such as a nurse or physician, and may be one of various types of safety syringe, pen-injector, or auto-injector. The injection device 1 can include a cartridge-based system that requires piercing a sealed ampule before use. Volumes of medicament delivered with these various devices can range from about 0.5 ml to about 2 ml. The injection device 1 may be a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml). In combination with a specific medicament, the injection device 1 may also be customized in order to operate within required specifications. For example, the injection device 1 may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, the injection device 1 may include a hollow needle ranging from about 25 to about 31 Gauge in size. Common sizes are 27 and 29 Gauge.

The injection device 1 can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of such an injection device 1 may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to allow injection of a medicament to be provided. The injection device 1 may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. The injection device 1 may also require a specific sequence of steps to cause the one or more automated functions to occur. The injection device 1 may operate with a sequence of independent steps.

The injection device 1 can include one or more functions of a safety syringe, pen-injector, or auto-injector. For example, the injection device 1 may include a mechanical energy source configured to automatically inject a medicament (as typically found in an auto-injector) and a dose setting mechanism (as typically found in a pen-injector).

The injection device 1 may be disposable or it may be re-usable.

The injection device 1 may provide a fixed dose or a user-settable dose.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly (A21), Arg (B31), Arg (B32) human insulin (insulin glargine); Lys (B3), Glu (B29) human insulin; Lys (B28), Pro (B29) human insulin; Asp (B28) human insulin; human insulin, wherein proline in position B28 is replaced by Asp, Lys, Leu, Val or Ala and wherein in position B29 Lys may be replaced by Pro; Ala (B26) human insulin; Des (B28-B30) human insulin; Des (B27) human insulin and Des (B30) human insulin.

Exemplary insulin derivatives are, for example, B29-N-myristoyl-des (B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des (B30) human insulin; B29-N-(N-lithocholyl-gamma-glutamyl)-des (B30) human insulin; B29-N-(ω-carboxyheptadecanoyl)-des (B30) human insulin and B29-N-(ω-carboxyhepta-decanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091 March-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term “antibody”, as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms “fragment” or “antibody fragment” refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms “Complementarity-determining region” or “CDR” refer to short polypeptide sequences within the variable region of both heavy and light chain polypeptides that are primarily responsible for mediating specific antigen recognition. The term “framework region” refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1) (R2) (R3) (R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

The invention claimed is:

1. A data collection device, comprising:

a first portion attachable to a rotatable dosage knob of an injection device, wherein the rotatable dosage knob is configured to rotate as medicament is expelled from the injection device;

a second portion rotatably coupled with the first portion, wherein at least part of the second portion is movable axially relative to the first portion, the second portion comprising a button that is rotationally fixed, the button being moveable between an extended position and a depressed position, wherein moving the button to the depressed position causes the second portion to move axially relative to the first portion;

one or more sensors configured to detect rotation of the first portion relative to the second portion;

a processor configured to, based on a movement detected by the one or more sensors, determine a medicament amount expelled by the injection device; and a one-way mechanism engageable with the first portion and configured to permit relative rotational movement between the button and the first portion in a first rotational direction during dose delivery and to prevent relative rotational movement between the button and the first portion in a second rotational direction opposite the first rotational direction during dose delivery.

2. The data collection device according to claim 1, wherein the one-way mechanism comprises a ratchet surface on the first portion and at least one follower element on the second portion or the ratchet surface on the second portion and the at least one follower element on the first portion, and the at least one follower element engageable with the ratchet surface.

3. The data collection device according to claim 2, wherein the at least one follower element is biased into engagement with the ratchet surface at least when the button is in the depressed position, and the at least one follower element is deflectable by moving across the ratchet surface.

4. The data collection device according to claim 3, wherein the at least one follower element comprises a resilient arm.

5. The data collection device according to claim 3, wherein the at least one follower element biases the button towards the extended position.

6. The data collection device according to claim 2, wherein the ratchet surface is on the button.

7. The data collection device according to claim 2, wherein the at least one follower element is provided on a follower member which is a separate component from the first and second portions.

8. The data collection device according to claim 7, wherein the follower member comprises a battery holder.

9. The data collection device according to claim 1, further comprising a biasing member configured to bias the button into the extended position.

10. The data collection device according to claim 1, wherein the one-way mechanism is configured to change between an engaged position in which rotation of the button relative to the first portion in the second rotational direction is prevented, and a disengaged position in which the button is freely rotatable relative to first portion, and wherein movement of the button from the extended position towards the depressed position moves the one-way mechanism from the disengaged position to the engaged position.

11. The data collection device according to claim 10, wherein the one-way mechanism comprises a ratchet surface on the first portion and at least one follower element on the second portion or the ratchet surface on the second portion and the at least one follower element on the first portion, and the at least one follower element engageable with the ratchet surface; and wherein when the one-way mechanism is in the engaged position, the at least one follower element is in engagement with the ratchet surface, and when the one-way mechanism is in the disengaged position, the at least one follower element is out of engagement with the ratchet surface.

12. The data collection device according to claim 1, further comprising a power source and a switch configured to connect the power source to the processor to transition the device between a deactivated state and an activated state, and wherein a movement of the button towards the depressed position causes the switch to render the device in the activated state.

13. A medicament administration apparatus, comprising:

an injection device comprising a rotatable component configured to rotate as a medicament is expelled from the injection device; and a data collection device, the data collection device comprising:

a first portion attachable to the rotatable component of the injection device;

a second portion rotatably coupled with the first portion, wherein at least part of the second portion is movable axially relative to the first portion, the second portion comprising a button that is rotationally fixed, the button being moveable between an extended position and a depressed position, wherein moving the button to the depressed position causes the second portion to move axially relative to the first portion;

one or more sensors configured to detect rotation of the first portion relative to the second portion;

a processor configured to, based on a movement detected by the one or more sensors, determine a medicament amount expelled by the injection device; and a one-way mechanism engageable with the first portion and configured to permit relative rotational movement between the button and the first portion in a first rotational direction during dose delivery and to prevent relative rotational movement between the button and the first portion in a second rotational direction opposite the first rotational direction during dose delivery.

14. The medicament administration apparatus according to claim 13, wherein:

the injection device comprises an injection button arranged to cause expulsion of the medicament from the injection device; and the second portion of the data collection device is arranged to press on the injection button when pressure is applied to the button of the data collection device.

15. The medicament administration apparatus according to claim 13, wherein the injection device further comprises a container of medicament.

16. The medicament administration apparatus according to claim 13, wherein the one-way mechanism comprises a ratchet surface on the first portion and at least one follower element on the second portion or the ratchet surface on the second portion and the at least one follower element on the first portion, and the at least one follower element engageable with the ratchet surface.

17. The medicament administration apparatus according to claim 16, wherein the at least one follower element is biased into engagement with the ratchet surface at least when the button is in the depressed position, and the at least one follower element is deflectable by moving across the ratchet surface.

18. The medicament administration apparatus according to claim 16, wherein the at least one follower element comprises a resilient arm.

19. The medicament administration apparatus according to claim 16, wherein the ratchet surface is on the button of the data collection device.

20. The medicament administration apparatus according to claim 16, wherein the at least one follower element is provided on a follower member which is a separate component from the first and second portions, and wherein the follower member comprises a battery holder.

* * * * *